United States Patent
Soares Da Silva et al.

(10) Patent No.: US 12,129,247 B2
(45) Date of Patent: Oct. 29, 2024

(54) ADMINISTRATION REGIME FOR NITROCATECHOLS

(71) Applicant: BIAL-PORTELA & CA, S.A., São Mamede do Coronado (PT)

(72) Inventors: Patricio Manuel Vieira Araujo Soares Da Silva, São Mamede do Coronado (PT); Teresa Lucia Silva Pereira Nunes, São Mamede do Coronado (PT); Lyndon Christopher Wright, São Mamede do Coronado (PT); Pedro Nuno Leal Palma, São Mamede do Coronado (PT); David Alexander Learmonth, São Mamede do Coronado (PT)

(73) Assignee: BIAL-PORTELA & CA, S.A., S. Mamede Do Coronado (PT)

( * ) Notice: Subject to any disclaimer, the term of this patent is extended or adjusted under 35 U.S.C. 154(b) by 82 days.

(21) Appl. No.: 16/114,430

(22) Filed: Aug. 28, 2018

(65) Prior Publication Data

US 2019/0144436 A1    May 16, 2019

Related U.S. Application Data

(60) Division of application No. 13/963,621, filed on Aug. 9, 2013, now Pat. No. 10,065,944, which is a continuation of application No. 13/583,375, filed as application No. PCT/GB2011/052056 on Oct. 21, 2011, now abandoned.

(60) Provisional application No. 61/441,988, filed on Feb. 11, 2011.

(51) Int. Cl.
| | | |
|---|---|---|
| A61K 31/165 | (2006.01) | |
| A61K 31/198 | (2006.01) | |
| A61K 31/4439 | (2006.01) | |
| A61K 45/06 | (2006.01) | |
| C07D 413/12 | (2006.01) | |

(52) U.S. Cl.
CPC .......... C07D 413/12 (2013.01); A61K 31/165 (2013.01); A61K 31/198 (2013.01); A61K 31/4439 (2013.01); A61K 45/06 (2013.01)

(58) Field of Classification Search
CPC .......................... C07D 413/12; A61K 31/165
See application file for complete search history.

(56) References Cited

U.S. PATENT DOCUMENTS

| | | | |
|---|---|---|---|
| 1,532,178 | A | 4/1925 | Godbold |
| 3,647,809 | A | 3/1972 | Reiter et al. |
| 4,065,563 | A | 12/1977 | Narayanan et al. |
| 4,264,573 | A | 4/1981 | Powell et al. |
| 4,386,668 | A | 6/1983 | Parish |
| 4,963,590 | A | 10/1990 | Backstrom et al. |
| 5,236,952 | A | 8/1993 | Bernauer et al. |
| 5,476,875 | A | 12/1995 | Bernauer et al. |
| 5,633,371 | A | 5/1997 | Bernauer et al. |
| 5,705,703 | A | 1/1998 | Bernauer et al. |
| 5,840,769 | A | 11/1998 | Kolter et al. |
| 6,206,110 | B1 | 3/2001 | Slaughter, Jr. et al. |
| 6,361,794 | B1 | 3/2002 | Kushla et al. |
| 6,500,867 | B1 | 12/2002 | Virkki et al. |
| 6,509,363 | B2 | 1/2003 | Salituro et al. |
| 6,512,136 | B1 | 1/2003 | Benes et al. |
| 6,521,136 | B1 | 2/2003 | Sfez et al. |
| 6,627,646 | B2 | 9/2003 | Bakale et al. |
| 6,660,753 | B2 | 12/2003 | Van Wagenen et al. |
| 7,041,685 | B2 | 5/2006 | Cai et al. |
| 7,112,595 | B2 | 9/2006 | Wagenen et al. |
| 7,144,876 | B2 | 12/2006 | Cai et al. |
| 7,317,029 | B2 | 1/2008 | Cai et al. |

(Continued)

FOREIGN PATENT DOCUMENTS

| | | |
|---|---|---|
| CN | 1340500 A | 3/2002 |
| CN | 1173926 C | 11/2004 |

(Continued)

OTHER PUBLICATIONS

Guidance for Industry, Food-Effect Bioavailability and Fed Bioavailability Studies, by US DHHS, FDA, CDER, Dec. 2002.*
Bonelli et al., A systematic review of the treatment studies in Huntington's disease since 1990, Expert Opinion on Pharmacotherapy, 8:2, 141-153.*

(Continued)

*Primary Examiner* — Svetlana M Ivanova
(74) *Attorney, Agent, or Firm* — McCarter & English, LLP; Steven G. Davis; Wei Song (57) ABSTRACT

A compound of formula (I)

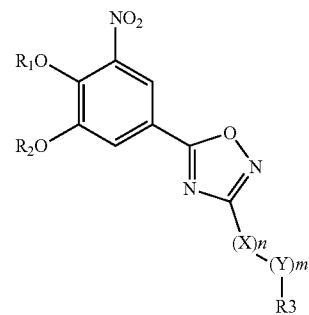

where $R_1$, $R_2$, X, Y, n, m, $R_3$, $R_4$, $R_5$, $R_6$ and $R_7$ are as defined herein, for use in the prophylaxis or treatment of a central and peripheral nervous system disorder, wherein the compound of formula (I) is administered prior to sleep, before bedtime or at bedtime.

17 Claims, 3 Drawing Sheets

(56) References Cited

U.S. PATENT DOCUMENTS

| | | | |
|---|---|---|---|
| 7,435,750 B2 | 10/2008 | Cai et al. | |
| 7,553,964 B2 | 6/2009 | Liu et al. | |
| 8,168,793 B2 | 5/2012 | Learmonth et al. | |
| 8,524,746 B2 | 9/2013 | Learmonth et al. | |
| 8,536,203 B2 | 9/2013 | Learmonth et al. | |
| 8,907,099 B2 | 12/2014 | Learmonth et al. | |
| 8,975,410 B2 | 3/2015 | Learmonth et al. | |
| 9,126,988 B2 | 9/2015 | Russo et al. | |
| 9,132,094 B2 | 9/2015 | Cardoso de Vasconcelos et al. | |
| 9,446,012 B2 | 9/2016 | Learmonth et al. | |
| 9,550,759 B2 | 1/2017 | Learmonth et al. | |
| 9,630,955 B2 | 4/2017 | Russo et al. | |
| 9,745,290 B2 | 8/2017 | Learmonth et al. | |
| 10,065,944 B2 * | 9/2018 | Soares Da Silva | A61K 31/4439 |
| 10,071,085 B2 | 9/2018 | de Vasconcelos et al. | |
| 10,583,130 B2 | 3/2020 | de Vasconcelos et al. | |
| 2002/0012701 A1 | 1/2002 | Kolter et al. | |
| 2003/0055085 A1 | 3/2003 | Wagenen et al. | |
| 2004/0097555 A1 | 5/2004 | Ohkawa et al. | |
| 2004/0138281 A1 | 7/2004 | Wikstrom et al. | |
| 2004/0171645 A1 | 9/2004 | Bartoszyk et al. | |
| 2006/0019956 A1 | 1/2006 | Green | |
| 2006/0160812 A1 | 7/2006 | Schubert et al. | |
| 2006/0173074 A1 | 8/2006 | Ellmen et al. | |
| 2006/0257473 A1 | 11/2006 | Puranajoti | |
| 2007/0013830 A1 | 1/2007 | Hayakawa | |
| 2007/0026054 A1 | 2/2007 | Theobald et al. | |
| 2007/0048384 A1 | 3/2007 | Rosenberg et al. | |
| 2007/0078133 A1 | 4/2007 | Liu et al. | |
| 2007/0117165 A1 | 5/2007 | Presnell et al. | |
| 2007/0219187 A1 | 9/2007 | Bessis et al. | |
| 2007/0299110 A1 | 12/2007 | Gagliardi et al. | |
| 2008/0051441 A1 | 2/2008 | Brown et al. | |
| 2008/0071184 A1 | 3/2008 | Carter | |
| 2008/0167286 A1 | 7/2008 | Gopalakrishnan et al. | |
| 2008/0269236 A1 | 10/2008 | Ji et al. | |
| 2009/0000437 A1 | 1/2009 | Johnson et al. | |
| 2009/0054437 A1 | 2/2009 | Learmonth et al. | |
| 2009/0111778 A1 | 4/2009 | Apodaca et al. | |
| 2009/0162283 A1 | 6/2009 | Bando et al. | |
| 2009/0227626 A1 | 9/2009 | Deraeve et al. | |
| 2009/0312347 A1 | 12/2009 | Dahl et al. | |
| 2010/0004284 A1 | 1/2010 | Farina et al. | |
| 2010/0113529 A1 * | 5/2010 | Learmonth | A61K 31/4439 514/340 |
| 2010/0168113 A1 | 7/2010 | Learmonth et al. | |
| 2010/0256193 A1 | 10/2010 | Cardoso de Vasconcelos et al. | |
| 2010/0256194 A1 | 10/2010 | Cardoso de Vasconcelos et al. | |
| 2010/0266193 A1 | 10/2010 | Park | |
| 2011/0014282 A1 | 1/2011 | de Vasconcelos | |
| 2011/0112301 A1 | 5/2011 | Learmonth et al. | |
| 2011/0301204 A1 | 12/2011 | de Almeida et al. | |
| 2012/0196904 A1 | 8/2012 | Learmonth et al. | |
| 2013/0324578 A1 | 12/2013 | Soares Da Silva et al. | |
| 2013/0331416 A1 | 12/2013 | Learmonth et al. | |
| 2014/0024682 A1 | 1/2014 | Learmonth et al. | |
| 2014/0045900 A1 | 2/2014 | Soares Da Silva et al. | |
| 2014/0350057 A1 | 11/2014 | Russo et al. | |
| 2015/0072977 A1 | 3/2015 | Learmonth et al. | |
| 2015/0166519 A1 | 6/2015 | Learmonth | |
| 2015/0359783 A1 | 12/2015 | de Vasconcelos et al. | |
| 2016/0009699 A1 | 1/2016 | Learmonth et al. | |
| 2016/0009700 A1 | 1/2016 | Russo et al. | |
| 2017/0340593 A1 | 11/2017 | Soares da Silva et al. | |
| 2017/0362213 A1 | 12/2017 | Learmonth et al. | |
| 2019/0008774 A1 | 1/2019 | Cardoso de Vasconcelos et al. | |
| 2020/0078328 A1 | 3/2020 | Soares Da Silva et al. | |
| 2020/0102295 A1 | 4/2020 | Learmonth et al. | |
| 2021/0023067 A1 | 1/2021 | De Vasconcelos et al. | |
| 2021/0186910 A1 | 6/2021 | Soares Da Silva et al. | |
| 2021/0315824 A1 | 10/2021 | Cardoso de Vasconcelos et al. | |

FOREIGN PATENT DOCUMENTS

| | | | |
|---|---|---|---|
| DE | 3740383 A1 | 6/1988 | |
| EP | 0237929 A1 | 9/1987 | |
| EP | 0372654 A2 | 6/1990 | |
| EP | 0462639 A1 | 12/1991 | |
| EP | 0487774 A1 | 6/1992 | |
| EP | 1167342 A1 | 1/2002 | |
| EP | 1845097 A1 | 10/2007 | |
| EP | 1881979 A1 | 1/2008 | |
| FR | 1260080 A | 5/1961 | |
| JP | H10-67651 A | 3/1998 | |
| JP | 2002-020319 A | 1/2002 | |
| JP | 2003-116966 A | 4/2003 | |
| JP | 2004-115374 A | 4/2004 | |
| JP | 2007-506797 A | 3/2007 | |
| JP | 2008-509195 A | 3/2008 | |
| JP | 2008-162955 A | 7/2008 | |
| JP | 2011-500506 A | 1/2011 | |
| JP | 2012-522764 A | 9/2012 | |
| JP | 2014-505096 A | 2/2014 | |
| WO | 1993/13083 A1 | 7/1993 | |
| WO | 1998/32425 A1 | 7/1998 | |
| WO | 1999/48484 A2 | 9/1999 | |
| WO | 2000/37423 A1 | 6/2000 | |
| WO | 2001/12627 A1 | 2/2001 | |
| WO | 2001/68083 A1 | 9/2001 | |
| WO | 2002/051442 A1 | 7/2002 | |
| WO | 2002/060446 A1 | 8/2002 | |
| WO | 2002/068417 A2 | 9/2002 | |
| WO | 2002/096867 A2 | 12/2002 | |
| WO | 2002/100826 A2 | 12/2002 | |
| WO | 2004/058163 A2 | 7/2004 | |
| WO | 2005/013982 A1 | 2/2005 | |
| WO | 2005/044797 A1 | 5/2005 | |
| WO | 2005/105780 A2 | 11/2005 | |
| WO | 2006/061697 A1 | 6/2006 | |
| WO | 2006/071184 A1 | 7/2006 | |
| WO | 2006/114400 A1 | 11/2006 | |
| WO | 2006/129199 A1 | 12/2006 | |
| WO | 2006/132914 A2 | 12/2006 | |
| WO | 2007/013830 A1 | 2/2007 | |
| WO | 2007/034024 A2 | 3/2007 | |
| WO | 2007/113276 A1 | 10/2007 | |
| WO | 2007/117165 A1 | 10/2007 | |
| WO | 2008/021388 A1 | 2/2008 | |
| WO | WO-2008094053 A1 * | 8/2008 | A61K 31/4439 |
| WO | 2008/118331 A2 | 10/2008 | |
| WO | 2009/029632 A1 | 3/2009 | |
| WO | 2009/116882 A1 | 9/2009 | |
| WO | 2010/014025 A1 | 2/2010 | |
| WO | 2010/114405 A2 | 10/2010 | |
| WO | 2011/107653 A2 | 9/2011 | |
| WO | 2012/107708 A1 | 8/2012 | |
| WO | 2013/089573 A1 | 6/2013 | |

OTHER PUBLICATIONS

Kandel, Schwartz and Jessell, Principles of Neural Science, Fourth Ed., Chapter 43, The Basal Ganglia, pp. 853-867, 2000.*

Robbins and Kaplan LLP Generically Speaking: a Hatch-Waxman Litigation Bulletin, May 16, 2018, regarding *Endo Pharms. Inc. v. Teva Pharms. USA, Inc.*, 2018 U.S. App. LEXIS 12961 (Fed. Cir. May 16, 2018), available at https://www.jdsupra.com/legalnews/endo-pharms-inc-v-teva-pharms-USA-inc-57720/.*

Kurth et al., Tolcapone improves motor function and reduces levodopa requirement in patients with Parkinson's disease experiencing motor fluctuations: a multicenter, double-blind, randomized, placebo-controlled trial, Neurology 1997; 48: 81-87.*

[No authors listed], COMT inhibitors, Movement Disorders, 2002; 17 (4): S45-S51.*

Center for Drug Evaluation and Research, Applicantion No. 20697, Pharmaceutical Reviews, Tasmar (Tolcapone), Hoffman-La Roche Inc, 53 pages, Jun. 3, 1996.*

Al-Mousawi et al., Alkylazinylcarbonitriles as building blocks in heterocyclic synthesis: a route for the synthesis of 4-methyl-2-oxopyridines. Pharmazie. 1999;54(8):571-574.

(56) References Cited

OTHER PUBLICATIONS

Al-Omran et al., Heterocyclic Synthesis via Enaminones: Novel Synthesis of (1 H)-Pyridin-2-one, Pyrazolo [1 ,5-?] pyrimidine and Isoxazole Derivatives Incorporating a N-Methylphthalimide and Their Biological Evaluation. J Heterocyclic Chem. Mar. 2005;42:307-312.
Ansel et al., Pharmaceutical Dosage Forms and Drug Delivery Systems, 6th edition, pp. 192-203 (1995).
Bondavalli et al., An Efficient Synthesis of Functionalized 2-Pyridones by Direct Route or via Amide/Enolate Ammonium Salt Intermediates. Synthesis. 1999;7:1169-1174.
Bonifati et al., New, selective catechol-O-methyltransferase inhibitors as therapeutic agents in Parkinson's disease. Pharmacol Ther. Jan. 1999;81(1):1-36.
Bonifácio et al., Brain and peripheral pharmacokinetics of levodopa in the cynomolgus monkey following administration of opicapone, a third generation nitrocatechol COMT inhibitor. Neuropharmacology. Feb. 2014;77:334-41.
Caplus Accession No. 2003:365244. Preparation of substituted benzamide derivatives as inhibitors of phosphodiesterase IV. 1 page. (2010).
Caplus Accession No. 2006:236916. Dmitriyeva et al., Features of the reaction of some 2-chloronicotinonitriles with hydroxylamine. Synthesis of 3-(1, 2, 4-oxadiazol-3yl)pyridines and their fragmentation under electron impact. IzvestiyaVysshikh UchehnykhZavedenii, Khimiya i Khimicheskaya Tekhnologiya. 2005;48(11):14-17.
Costa et al., Opicapone long-term efficacy and safety in Parkinson's disease BIPARK-II study: a one-year open-label follow-up. European Journal of Neurology. 2014;21(Suppl. 1):171. Abstract No. eP1259.
Davies et al., A general [3 + 2 + 1] annulation strategy for the preparation of pyridine N-oxides. Org Lett. Jan. 25, 2001;3(2):209-11.
Dutrow, X-ray Powder Diffraction (XRD). excerpt, http://serc.carleton.edu/research_education/geochemsheets/techniques/XRD.html posted Aug. 2008, retrieved from Internet Archive Wayback Machine May 11, 2016. 2 pages.
Ferreira et al., Effect of opicapone multiple-dose regimens on levodopa pharmacokinetics, motor response, and erythrocyte-COMT activity in Parkinson's patients co-administered with levodopa/dopa-decarboxylase inhibitor. Journal of Neurological Sciences. 2013;333:e116. vol. 333, Abstract No. 1034.
Girges et al., Synthesis of Nicotinoyl Hydrazones, Their N-Oxide Analogues and the Corresponding 3-(5-Aryl-1,3,4-oxadiazol-2-yl)pyridine Derivatives as Potential Hypoglycemic Agents. Chem Papers. 1992;46(4):272-277.
Grosset et al., Parkinson's Disease, Clinician's Desk Reference, Manson Publishing, 2009, p. 62.
Howse et al., Brocresine in Parkinson's disease. Action of a peripheral and central decarboxylase inhibitor in potentiating levodopa. J Neurol Neurosurg Psychiatry. Feb. 1973;36(1):27-9.
Ivanova, Technology of dosage forms. Moscow, Medicine, vol. 2, 1991, pp. 223-224. English translation.
Kiss et al., Discovery of a long-acting, peripherally selective inhibitor of catechol-O-methyltransferase. J Med Chem. Apr. 22, 2010;53(8):3396-411.
Korolkovas, Essentials of Medicinal Chemistry, Second Edition. John Wiley & Sons, New York. pp. 97-103 and 135-137 (1988).
Kristensen et al., Granulation, A Review on Pharmaceutical Wet-Granulation. Drug Development and Industrial Pharmacy. 1987;13(4 &5):803-872.
Krogsgaard-Larsen et al., Bioreversible Derivatives for Various Functional Groups. Textbook of Drug Design and Discovery, Third Edition. Taylor & Francis Inc., London. Table 14.3, pp. 426-427 (2002).
Kubinyi, 3D QSAR in Drug Design, Theory Methods and Applications. Kluwer/Escom, pp. 243-244, (1998).
Learmonth et al., Chemical synthesis and characterization of conjugates of a novel catechol-O-methyltransferase Inhibitor. Bioconjug Chem. Sep.-Oct. 2002;13(5):1112-8.
Lees et al., Efficacy and safety of opicapone, a new COMT-inhibitor, for the treatment of motor fluctuations in Parkinson's Disease patients: BIPARK-II study. Journal of Neurological Sciences. 2013;333:e116. Abstract No. 1038.
Madopar, Instructions for use, found on-line Jun. 28, 2016; URL:http://www.webvidal.ru/2010/drug/LP_18271.htm; Feb. 2, 2011.
Marcoux et al., A general preparation of pyridines and pyridones via the annulation of ketones and esters. J Org Chem. Jun. 15, 2001;66(12):4194-9.
Masjost et al., Structure-Based Design, Synthesis, and in vitro Evaluation of Bisubstrate Inhibitors for Catechol O-Methyltransferase (COMT). Chem Eur J. 2000;6(6):971-982.
Nutt et al., Pharmacokinetics of levodopa. Clin Neuropharmacol. 1984;7(1):35-49.
Nutt, Catechol-O-methyltransferase inhibitors for treatment of Parkinson's disease. Lancet. Apr. 25, 1998;351(9111):1221-2.
Parashos et al., Frequency, reasons, and risk factors of entacapone discontinuation in Parkinson disease. Clin Neuropharmacol. May-Jun. 2004;27(3):119-23.
Parkinson, Stellenwert von COMT-Hemmern Bestatigt. MMW, Fortschritte der Medizin. May 2001;18:51.
Pedrosa et al., Oxidative and non-oxidative mechanisms of neuronal cell death and apoptosis by L-3,4-dihydroxyphenylalanine (L-DOPA) and dopamine. Br J Pharmacol. Dec. 2002;137(8):1305-13.
Poulain et al., Parallel synthesis of 1,2,4-oxadiazoles from carboxylic acids using an improved, uranium-based, acitvation. Tetrahedron Letters. 2001;42:1495-1498.
Rasenack et al., Micron-size drug particles: common and novel micronization techniques. Pharm Dev Technol. 2004;9(1):1-13.
Reagan-Shaw et al., Dose translation from animal to human studies revisited. FASEB J. Mar. 2008;22(3):659-61.
Reches et al., 3-o-methyldopa inhibits rotations induced by levodopa in rats after unilateral destruction of the higrostriatal pathway. Neurology. Aug. 1982;32(8):887-8.
Rocha et al., Effect of opicapone and entacapone upon levodopa pharmacokinetics during three daily levodopa administrations. Eur J Clin Pharmacol. Sep. 2014;70(9):1059-71.
Smith et al., In vitro metabolism of tolcapone to reactive intermediates: relevance to tolcapone liver toxicity. Chem Res Toxicol. Feb. 2003;16(2):123-8.
Soares-Da-Silva et al., The O-methylated derivative of L-DOPA, 3-O-methyl-L-DOPA, fails to inhibit neuronal and hon-neuronal aromatic L-amino acid decarboxylase. Brain Res. Apr. 28, 2000;863(1-2):293-7.
Tervo et al., A structure-activity relationship study of catechol-O-methyltransferase inhibitors combining molecular docking and 3D QSAR methods. J Comput Aided Mol Des. Dec. 2003;17(12):797-810.
Tohgi et al., The significance of 3-O-methyldopa concentrations in the cerebrospinal fluid in the pathogenesis of wearing-off phenomenon in Parkinson's disease. Neurosci Lett. Oct. 28, 1991;132(1):19-22.
Vieira-Coelho et al., Effects of tolcapone upon soluble and membrane-bound brain and liver catechol-O-methyltransferase. Brain Res. Mar. 6, 1999;821(1):69-78.
Wermuth, The Practice of Medicinal Chemistry, 2nd Edition. Chapters 9-10, pp. 131-145, 147-157 (2003).
Wikberg et al., Identification of major metabolites of the catechol-O-methyltransferase inhibitor entacapone in rats and humans. Drug Metab Dispos. Jan.-Feb. 1993;21(1):81-92.
Wikipedia. Bioavailability. retrieved online at: https://en.wikipedia.org/w/index.php?title=Bioavailability&oldid=411623071> Oct. 24, 2016. 7 pages.
Wikipedia. COMT inhibitor. retrieved online at: http://en.wikipedia.org/w/index.php?title=COMT_inhibitor&oldid=478541384. Feb. 24, 2012. 1 page.
www.ip.com, PriorArtDatabse, Technical Disclosure. [1,2,4]-oxadazolyl nitrocatechol derivatives. IP.com No. IPCOM000217126D. May 3, 2012. 12 pages.
European Search Report for Application No. 06075343.1, dated Apr. 19, 2006, 5 pages.
International Preliminary Report on Patentability for Application No. PCT/PT2006/000020, dated Jan. 29, 2008.

(56) References Cited

OTHER PUBLICATIONS

International Preliminary Report on Patentability for Application No. PCT/PT2007/000016, dated Oct. 14, 2008.
International Preliminary Report on Patentability for Application No. PCT/PT2007/000043, dated Aug. 4, 2009.
U.S. Appl. No. 15/402,607, filed Jan. 10, 2017, 2017-0362213.
U.S. Appl. No. 14/814,603, filed Jul. 31, 2015, U.S. Pat. No. 9,630,955.
U.S. Appl. No. 15/528,886, filed May 23, 2017, 2017-0340593.
U.S. Appl. No. 13/583,375, filed Aug. 11, 2013, 2014-0045900.
U.S. Appl. No. 13/963,621, filed Aug. 9, 2013, 2013-0324578.
International Preliminary Report on Patentability for Application No. PCT/PT2009/000044, dated Feb. 10, 2011.
International Search Report and Written Opinion for Application No. PCT/PT2006/000020, dated Nov. 8, 2006.
International Search Report and Written Opinion for Application No. PCT/PT2007/000016, dated Jul. 13, 2007, 12 pages.
International Search Report and Written Opinion for Application No. PCT/PT2007/000043, dated Apr. 23, 2008.
International Search Report and Written Opinion for Application No. PCT/PT2009/000044, dated Nov. 16, 2009, 16 pages.
Center for Drug Evaluation and Research, Application No. 20697, Pharmaceutical Reviews. Tasmar (tolcapone). Hoffman-La Roche Inc. 53 pages, Jun. 3, 1996.
Chozai To Joho, Drug Preparation and Information. Comtan Tablets 100 mg. 2007;13(7):51-55.
Drug Interview Form, Comtan Tablets 100mg. 41 pages (2015).
Japanese Office Action for Application No. 2019-142271, dated Jul. 28, 2020, 8 pages.
Aldakheel et al., Pathogenesis-Targeted, Disease-Modifying Therapies in Parkinson Disease. Neurotherapeutics. 2014;11:6-23.
Carnegie Mellon, CMU Seed Fund Project on Detection and Control of Pharmaceutical Polymorphism. Carnegie Mellon, The Department of Physics. Retrieved online at: http://andrew.cmu/edu/user/suter/polymorph.html. 3 pages. (2002).
De Gruyter, Concise Encyclopedia Chemistry. Bibliographisches Institut & F.A. Brockhaus AG, Mannheim. Dr. Hans-Dieter Jakubke (Ed.). pp. 872-873, (1993).
Doelker, Crystalline modifications and polymorphism changes during drug manufacture. Ann Pharm Fr. May 2002;60(3):161-76.
Doelker, Physicochemical behavior of active substances. Consequences for the feasibility of pharmaceutical forms. S.T.P. Pharma Pratiques. 1999;9(5):399-409, including CAPLUS abstract, AN:2000:10870.
Jain et al., Polymorphism in Pharmacy. Indian Drugs. 1986;23(6):315-329.
Mcghee et al., A systematic review of biomarkers for disease progression in Parkinson's disease. BMC Neurology. 2013;13;35, 13 pages, (2013).
Mlakar et al., Carboxamide Oximes as Convenient Precursors for the Synthesis of Pyrimidine N-Oxides. Tetrahedron. 1998;54:4387-4396.
Muzaffar et al., Polymorphism and Drug Availability. Journal of Pharmacy (Lahore). 1979;1(1):59-66.
Otsuka et al., Effect of Polymorphic Forms of Bulk Powders on Pharmaceutical Properties of Carbamazepine Granules. Chem Pharm Bull. 1999;47(6):852-6.
Singhal et al., Drug polymorphism and dosage form design: a practical perspective. Adv Drug Deliv Rev. Feb. 23, 2004;56(3):335-47.
Sun et al., Particle Size Specifications for Solid Oral Dosage Forms: A Regulatory Perspective. American Pharmaceutical Review. 8 pages, May 1, 2010.
Taday et al., Using Terahertz pulse spectroscopy to study the crystalline structure of a drug: a case study of the polymorphs of ranitidine hydrochloride. J Pharm Sci. Apr. 2003;92(4):831-8.
The Merck Manual, 18th Edition. pp. 1997-2001, (2007).
U.S. Pharmacopia #23, National Formulary #18. X-Ray Diffraction. (941), pp. 1843-1844, (1995).
Yoshii, How to use L-dopa modifiers (COMT inhibitors, MAOB inhibitors, zonisamide)Mebio. 2013;30(11):31-39.
U.S. Appl. No. 11/989,447, filed Jul. 26, 2006, U.S. Pat. No. 8,168,793.
U.S. Appl. No. 13/442,356, filed Apr. 9, 2012, U.S. Pat. No. 8,907,099.
U.S. Appl. No. 14/541,654, filed Nov. 14, 2014, U.S. Pat. No. 9,550,759.
U.S. Appl. No. 15/402,607, filed Jan. 10, 2017, U.S. Pat. No. 10,336,740.
U.S. Appl. No. 16/452,845, filed Jun. 26, 2019, 2020-0102295.
U.S. Appl. No. 13/002,287, filed Jul. 7, 2011, 2011-0301204.
U.S. Appl. No. 12/226,260, filed May 28, 2009, U.S. Pat. No. 8,536,203.
U.S. Appl. No. 14/014,548, filed Aug. 30, 2013, U.S. Pat. No. 9,446,012.
U.S. Appl. No. 12/524,848, filed Dec. 30, 2009, U.S. Pat. No. 8,524,746.
U.S. Appl. No. 13/950,661, filed Jul. 25, 2013, 2013-0331416.
U.S. Appl. No. 14/689,397, filed Apr. 17, 2015, U.S. Pat. No. 9,745,290.
U.S. Appl. No. 14/365,265, filed Jun. 13, 2014, U.S. Pat. No. 9,126,988.
U.S. Appl. No. 14/814,603, filed Jul. 31, 2015, U.S. Pat. No. 9,360,955.
U.S. Appl. No. 15/528,886, filed May 23, 2017, U.S. Pat. No. 10,357,468.
U.S. Appl. No. 16/513,703, filed Jul. 17, 2019, 2020-0078328.
U.S. Appl. No. 17/010,601, filed Sep. 2, 2020, 2021-0186910.
U.S. Appl. No. 13/963,621, filed Aug. 9, 2013, U.S. Pat. No. 10,065,944.
U.S. Appl. No. 12/750,956, filed Mar. 21, 2010, U.S. Pat. No. 9,132,094.
U.S. Appl. No. 14/825,600, filed Aug. 13, 2015, U.S. Pat. No. 10,071,085.
U.S. Appl. No. 16/050,602, filed Jul. 31, 2018, U.S. Pat. No. 10,583,130.
U.S. Appl. No. 16/809,662, filed Mar. 5, 2020, 2021-0023067.
U.S. Appl. No. 12/750,957, filed Mar. 31, 2010, 2010-0256194.
U.S. Appl. No. 16/122,643, filed Sep. 5, 2018, 2019-0008774.
U.S. Appl. No. 17/122,013, filed Dec. 15, 2020, 2021-0315824.
U.S. Appl. No. 13/583,375, filed Dec. 5, 2012, 2014-0045900.

\* cited by examiner

ADMINISTRATION REGIME FOR NITROCATECHOLS

This application is a divisional application of U.S. application Ser. No. 13/963,621, filed Aug. 9, 2013, which is a continuation of U.S. application Ser. No. 13/583,375, filed Sep. 7, 2012 and now abandoned, which, in turn, is a 35 U.S.C. § 371 national stage filing of International Application No. PCT/GB2011/052056, filed Oct. 21, 2011, which, in turn, claims priority to U.S. Provisional Application No. 61/441,988, filed Feb. 11, 2011. The entire contents of each of the aforementioned applications are incorporated herein by reference.

This invention relates to the use of substituted nitrocatechols of formula (I) in the treatment of central and peripheral nervous system disorders according to a specified administration (dosing) regimen (regime).

The rationale for the use of COMT inhibitors as adjuncts to levodopa/aromatic L-amino acid decarboxylase inhibitor (AADCi) therapy is based on their ability to reduce metabolic O-methylation of levodopa to 3-O-methyl-levodopa (3-OMD). The duration of levodopa-induced clinical improvement is brief as a result of the short in vivo half-life of levodopa which contrasts with the long half-life of 3-OMD. Additionally, 3-OMD competes with levodopa for transport across the blood-brain barrier (BBB), which means that only a very limited amount of an orally administered dose of levodopa actually reaches the site of action, i.e. the brain. Commonly, within only a few years of starting levodopa therapy with the usual administration regime, levodopa-induced clinical improvement declines at the end of each dose cycle, giving rise to the so-called 'wearing-off' pattern of motor fluctuations. A close relationship between the 'wearing-off' phenomenon and accumulation of 3-OMD has been described (Tohgi, H., et al., Neurosci. Letters, 132:19-22, 1992). It has been speculated that this may result from impaired brain penetration of levodopa due to competition for the transport system across the BBB with 3-OMD (Reches, A. et al., Neurology, 32:887-888, 1982) or more simply that there is less levodopa available to reach the brain (Nutt, J. G., Fellman, J. H., Clin. Neuropharmacol., 7:35-49, 1984). In effect, COMT inhibition protects levodopa from O-methylation metabolic breakdown in the periphery, and particularly in the intestine, such that with repeated doses of levodopa, the mean plasma levodopa concentration is raised. In addition to reduced competition for transport into the brain, a significantly greater percentage of the orally administered dose of levodopa is able to reach the site of action. Thus COMT inhibition serves to increase the bioavailability of levodopa and the duration of antiparkinsonian action is prolonged with single administrations of levodopa (Nutt, J. G., Lancet, 351:1221-1222, 1998).

The most potent COMT inhibitors reported thus far are 3,4-dihydroxy-4'-methyl-5-nitrobenzophenone (Tolcapone, Australian pat. AU-B-69764/87) and (E)-2-cyano-N,N-diethyl-3-(3,4-dihydroxy-5-nitrophenyl)acrylamide (Entacapone, German pat. DE 3740383 A1).

Although sharing essentially the same pharmacophore, tolcapone differs from entacapone in that it easily enters the central nervous systems (CNS) and is able to inhibit cerebral COMT as well as peripheral COMT. Shortly after its launch, tolcapone was withdrawn from the market after several cases of hepatotoxicity were reported including three unfortunate deaths from fatal fulminant hepatitis. Today tolcapone can only be used in Parkinsonian patients who are unresponsive to other treatments and only with regular monitoring of liver function, which is expensive and inconvenient for the patient. Although the actual mechanistic causes of the liver toxicity associated with tolcapone are not fully understood, in vitro studies have shown that tolcapone may be reduced metabolically to reactive intermediates and it has been speculated that these may form covalent adducts with hepatic proteins resulting in hepatocellular injury (Smith, K. S. et al, Chem. Res. Toxicol., 16:123-128, 2003).

Entacapone on the other hand, although sharing the same nitrocatechol pharmacophore with tolcapone, is not associated with liver toxicity and is generally regarded as a safe drug. Unfortunately, however, entacapone is a significantly less potent COMT inhibitor than tolcapone and has a much shorter in-vivo half-life. This means that entacapone has a very limited duration of effect and as a consequence, the drug must be administered in very high doses with every dose of levodopa taken by the patient. As such, the clinical efficacy of entacapone has been questioned—indeed a recent study (Parashos, S. A. et al., Clin. Neuropharmacol., 27(3): 119-123, 2004) revealed that the principal reason for discontinuation of entacapone treatment in Parkinson's disease patients was a perceived lack of efficacy.

Furthermore, the relatively short in-vivo half-life of known COMT inhibitors requires continuous treatment regimens normally involving the administration of several doses a day which many patients find to be burdensome. For example, tolcapone has to be administered three times a day. This factor can therefore interfere with patient compliance and quality of life.

Accordingly, there is still a need for COMT inhibitors exhibiting balanced properties of bioactivity, bioavailability and safety. In particular, there is a need for COMT inhibitors having a long in-vivo half-life and, thus, a prolonged action on COMT enabling fewer dosages to obtain the desired therapeutic effect.

The applicant has previously discovered compounds which, despite having a relatively short half life, are very potent COMT inhibitors endowed with exceptionally long duration of action compared to COMT inhibitors in the prior art (see WO2007/013830).

These compounds, which are shown hereinbelow as compounds of general formula (I), also markedly enhance the bioavailability of levodopa and increase the delivery of levodopa to the brain. The compounds significantly augment the levels of dopamine in the brain over a long period of time.

Even more surprisingly, the increased levels of levodopa are maintained steady over extended periods of time. These sustained effects upon both COMT activity and levodopa bioavailability after the administration of compounds of general formula (I) are markedly greater than those observed with tolcapone, the only COMT inhibitor thus far known to be endowed with a reasonably long duration of action. (Tolcapone has a terminal half life of around 2 hours and must be administered around 3 times per day.) Furthermore, compounds of general formula (I) produce a steady increase in levodopa delivery to the brain over extended periods of time, which contrasts with that observed with tolcapone, which is prone to induce marked oscillations in the brain delivery of levodopa. Thus compounds of general formula (I) are more likely to be endowed with therapeutic advantages due to sustained constant elevation of levodopa levels whilst the use of tolcapone is likely to induce undesirable side-effects such as dyskinesia due to abrupt increases and decreases in levodopa levels.

The present invention is based on a surprisingly advantageous administration regimen for the administration of the compounds of formula (I) which maximises the COMT inhibitory effect of the compounds.

Accordingly, in a first aspect the present invention relates to a compound of formula (I)

(I)

where $R_1$ and $R_2$ are the same or different and signify hydrogens, groups hydrolysable under physiological conditions, or optionally substituted alkanoyls or aroyls; X signifies a methylene group; Y represents O, S or NH; n represents 0, 1, 2 or 3; m represents 0 or 1; $R_3$ signifies a pyridine N-oxide group according to the formula A, B, or C, which is connected as indicated by the unmarked bond:

A

B

C where $R_4$, $R_5$, $R_6$ and $R_7$ are the same or different, and signify hydrogen, alkyl, thioalkyl, alkoxy, aryloxy, thioaryl, alkanoyl, aroyl, aryl, amino, alkylamino, dialkylamino, cycloalkylamino, heterocycloalkylamino, alkylsulphonyl, arylsulphonyl, halogen, haloalkyl, trifluoromethyl, cyano, nitro or heteroaryl; or two or more of $R_4$, $R_5$, $R_6$ and $R_7$ taken together signify aliphatic or heteroaliphatic rings or aromatic or heteroaromatic rings; the term 'alkyl', including its variant 'alk-' in terms such as 'alkoxy', 'alkanoyl' mean carbon residues, straight or branched, containing from one to six carbon atoms; the term 'aryl' means a phenyl or naph- thyl group; the term 'heterocycloalkyl' represents a four to eight-membered cyclic ring optionally incorporating at least one atom of oxygen, sulphur or nitrogen; the term 'heteroaryl' represents a five or six-membered ring incorporating at least one atom of sulphur, oxygen or nitrogen; the term 'halogen' represents fluorine, chlorine, bromine or iodine; and if $R_4$, $R_5$, $R_6$ and $R_7$ represent alkyl or aryl they are optionally substituted by one or more hydroxy, alkoxy or halogen groups; or a pharmaceutically acceptable salt, ester, carbamate or phosphate thereof;

for use in the prophylaxis or treatment of a central and peripheral nervous system disorder, wherein the compound of formula (I) is administered prior to sleep, before bedtime or at bedtime.

In a second aspect the present invention relates to a compound of formula (I)

(I)

where $R_1$ and $R_2$ are the same or different and signify hydrogens, groups hydrolysable under physiological conditions, or optionally substituted alkanoyls or aroyls; X signifies a methylene group; Y represents O, S or NH; n represents 0, 1, 2 or 3; m represents 0 or 1; $R_3$ signifies a pyridine N-oxide group according to the formula A, B, or C, which is connected as indicated by the unmarked bond:

A

B

C where $R_4$, $R_5$, $R_6$ and $R_7$ are the same or different, and signify hydrogen, alkyl, thioalkyl, alkoxy, aryloxy, thioaryl, alkanoyl, aroyl, aryl, amino, alkylamino, dialkylamino, cycloalkylamino, heterocycloalkylamino, alkylsulphonyl, arylsulphonyl, halogen, haloalkyl, trifluoromethyl, cyano, nitro or heteroaryl; or two or more of $R_4$, $R_5$, $R_6$ and $R_7$ taken together signify aliphatic or heteroaliphatic rings or aromatic or heteroaromatic rings; the term 'alkyl', including its variant 'alk-' in terms such as 'alkoxy', 'alkanoyl' mean carbon residues, straight or branched, containing from one to six carbon atoms; the term 'aryl' means a phenyl or naphthyl group; the term 'heterocycloalkyl' represents a four to eight-membered cyclic ring optionally incorporating at least one atom of oxygen, sulphur or nitrogen; the term 'heteroaryl' represents a five or six-membered ring incorporating at least one atom of sulphur, oxygen or nitrogen; the term 'halogen' represents fluorine, chlorine, bromine or iodine; and if $R_4$, $R_5$, $R_6$ and $R_7$ represent alkyl or aryl they are optionally substituted by one or more hydroxy, alkoxy or halogen groups; or a pharmaceutically acceptable salt ester, carbamate or phosphate thereof;

for use in the prophylaxis or treatment of a central and peripheral nervous system disorder, wherein the compound of formula (I) is administered without food and/or between intakes of food.

In a third aspect, the invention provides the use of a compound of formula (I) for the manufacture of a medicament for use in the prophylaxis or treatment of a central and peripheral nervous system disorder, wherein said compound is administered without food, between intakes of food, prior to sleep, before bedtime and/or at bedtime.

In a fourth aspect, the invention provide a method of prophylaxis or treatment of a central and peripheral nervous system disorder, comprising administering to a patient suffering from said disorder, without food, between intakes of food, prior to sleep, before bedtime and/or at bedtime a therapeutically effective amount of a compound of formula (I).

Surprisingly, the applicant has found that the compounds of formula (I) are advantageously administered to a patient who has a digestive system which is as free from food as possible. Therefore, the compounds of formula (I) should preferably be administered to a patient without food and/or between intakes of food e.g. between meals, prior to sleep, before bedtime or at bedtime. Administering the compound in this manner results in the compounds of formula (I) having better activity e.g. more long lasting and increased inhibition of COMT.

Further, as mentioned, the COMT inhibitors of formula (I) are used as an adjunct to catecholamine therapy, so that the metabolism of the catecholamine drug by COMT is decreased. The applicant has also surprisingly found that when a compound of formula (I) is administered to a patient already taking a catecholamine, such as levodopa (L-DOPA), the effects of the compound of formula (I) are improved if the compound of formula (I) is administered sequentially with the catecholamine. In particular, it has surprisingly been discovered that the compound of formula (I) adversely affects the bioavailability of levadopa, and levadopa adversely affects the bioavailability of the compound of formula (I). Consequently, according to the invention the compound of formula (I) is administered prior to sleep, before bedtime or at bedtime, before or after the last daily dose of levodopa has been given to the patient and before the following day's dosage of levodopa is administered. Therefore, the compound of formula (I) and the catecholamine drug are not within the patient's digestive system at the same time and/or not being substantially absorbed at the same time.

For the purpose of the present invention, last daily dose, last dose of the day, last daily administration and last administration of the day have the same meaning and can be used interchangeably.

The present invention will now be described with reference to the accompanying drawings.

As mentioned, because the compounds of formula (I) are extremely potent, they can potentially be administered in a single daily administration.

The compounds of formula (I) are preferably administered prior to sleep, before bedtime or at bedtime. The term 'prior to sleep' means that the compound of formula (I) is administered shortly before the patient goes to sleep, for example less than 90 minutes prior to sleep, particularly less than one hour prior to sleep, less than 30 minutes prior to sleep or immediately prior to sleep.

The term before bedtime (i.e. before going to bed) means particularly less than 90 minutes before going to bed, particularly less than 60 minutes before going to bed or less than 30 minutes before going to bed. The term at bedtime means less than 5 minutes before bedtime, for example on going to bed.

In other words, the compound of formula (I) is taken by the patient before the patient goes to bed (i.e. before bedtime or at bedtime), e.g. less than 90 minutes before bedtime, particularly less than 60 minutes before bedtime, less than 30 minutes before bedtime or less than 5 minutes before bedtime.

As will be clear in the context of the invention, the term 'prior to sleep' or 'before bedtime' does not mean any time in the day prior to sleep or going to bed, and in particular does not include, for example, 12 hours before sleep or going to bed. Rather this term means the drug is taken in the period close to the patient going to sleep and probably as part of the patient's bedtime routine.

In one embodiment, the compound of formula (I) is administered in combination therapy with a catecholamine drug. Preferably the catecholamine drug is levodopa.

As such, the administration regimen of the compound of formula (I) and the catecholamine drug may differ: each may be administered at the same time or at different times. It will therefore be appreciated that the compounds of the combination may be administered sequentially (e.g. before or after) or concomitantly, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The administration regime of each of the two or more compounds in a combination therapy may also differ with respect to the route of administration.

The applicant has surprisingly discovered that the compounds of formula (I) and the catecholamine drug each adversely affect the bioavailability of the other.

In particular, the compounds of formula (I) are administered prior to sleep, before bedtime or at bedtime, before or after the last administration of the day of the catecholamine drug and before the first administration of the next day of the catecholamine drug. This therefore avoids the adverse consequence each drug has on the bioavailability of the other. Preferably the COMT inhibitory activity of the compounds of formula I is active prior to administration of the catecholamine drug.

In one embodiment, the compound of formula (I) is administered from 30 to 150 minutes before or after the last daily administration of the catecholamine drug. For example the compound of formula (I) is administered at least 30-50 minutes, preferably at least one hour, before or after the last daily administration of the catecholamine drug. In another embodiment, the compound of formula (I) is administered at least one hour before or after the last daily administration of the catecholamine drug is administered, and preferably the compound of formula (I) is administered once daily at least one hour before or after the last daily administration of the catecholamine drug.

In embodiments of the invention there is a period of at least two, three, four, five or six hours between the administration of the catecholamine and the compounds of formula (I).

Preferably the subsequent administration of the catecholamine is administered at least two, more preferably at least three, and most preferably at least six hours after administration of the compound of formula (I). Suitably, the subsequent administration of the catecholamine is administered 12 hours or 23 hours after administration of the compound of formula (I). Preferably, the subsequent administration of the catecholamine drug is the first daily dose of catecholamine drug of the next day.

In addition, the administration regime according to the invention involves administration of the compound of formula (I) when the patient has a digestive system free from food. The applicant has discovered that the compounds of formula (I) have improved bioavailability when administered to a patient when the patient does not have food in their digestive system. In particular, the compound of formula (I) should be administered to the patient prior to sleep, before bedtime or at bedtime, without food after the patient has had their final meal of the day.

The term "a digestive system free from food" means that the part of the digestive system where most of the absorption of the compound of formula (I) occurs is free from food, e.g. stomach, small intestine (duodenum, jejunum, ileum).

In one embodiment of the invention the compound of formula (I) is administered at least one hour after the most recent intake of food and at least one hour before the next intake of food.

In one embodiment of the invention the compound of formula (I) is administered from 0.25 to 12 hours, preferably from 0.5 to 6 hours, more preferably from 0.75 to 4 hours, after an intake of food. In one embodiment of the invention the compound of formula (I) is administered after 0.25 to 10 hours overnight fasting.

In one embodiment of the invention, the compound of formula (I) is administered from 0.25 to 2 hours, preferably from 0.5 to 1.5 hours, before an intake of food.

Preferably the compound of formula (I) is administered prior to sleep, and more preferably less than one hour prior to sleep.

Most preferably, in order to avoid the interaction between the compound of formula (I) and the catecholamine drug, and also to administer the compound of formula (I) when the patient has a digestive system free of food, the compound of formula (I) is administered once daily prior to sleep, before bedtime or at bedtime.

As used herein, the term 'effective daily dose' is the effective daily amount of compound administered when administered according to the dosing periodicity.

In the present invention, effective daily doses of compounds of general formula (I) are in the range of about 1 to about 1200 mg/day, preferably about 1 to about 900 mg/day, more preferably about 5 to about 400 mg/day, even more preferably about 25 to about 300 mg/day, for example specific daily doses of 1 mg, 3 mg, 5 mg, 10 mg, 15 mg, 20 mg, 25 mg, 30 mg, 50 mg, 100 mg, 200 mg, 400 mg, 800 mg or 1200 mg.

As used herein, the term "dosage unit" refers to the amount of compound administered in each dosing periodicity.

It is preferred that individual dosage units of compounds of general formula (I) are in the range of about 1 to about 2400 mg, more preferably about 1 to about 1200 mg, even more preferably about 1 to about 800 mg, for example 1 mg, 3 mg, 5 mg, 10 mg, 15 mg, 20 mg, 25 mg, 30 mg, 50 mg, 100 mg, 200 mg, 400 mg, 800 mg or 1200 mg.

As mentioned above, COMT inhibitors are often used as adjuncts to catecholamine compounds because they reduce their metabolic O-methylation. In particular, COMT inhibitors are often used as adjuncts to levodopa/aromatic L-amino acid decarboxylase inhibitor (AADCi) therapy because they reduce metabolic O-methylation of levodopa to 3-O-methyl-levodopa (3-OMD).

Therefore, preferably, the pathological states treated by the compounds are central and peripheral nervous system-associated disorders of humans which benefit from administration of a COMT inhibitor.

When the compound of formula (I) is administered in combination with a catecholamine drug, it is possible that the catecholamine drug is administered sequentially or concomitantly with an AADCi, in particular carbidopa or benserazide.

The compounds of general formula (I), the catecholamine drug and the AADCi may be administered separately or in any combination. They may be administered concomitantly (for example, simultaneously) or sequentially, and with the same or differing dosing periodicity. For example, the compounds of the general formula (I) can be concomitantly or sequentially administered with the catecholamine drug.

The use of the compounds according to the invention is for the propylaxis or treatment of central and peripheral nervous system disorders. The central and peripheral nervous system disorder is, for example, a mood disorder, gastrointestinal disturbance, oedema formation state, hypertension or a movement disorder. Preferably, the disorders are movement disorders including disorders involving parkinsonism, Parkinson's Disease, and restless leg syndrome. The most preferred central and peripheral nervous system disorder is Parkinson's Disease.

As used herein, the term treatment and variations such as 'treat' or 'treating' refer to any regime that can benefit a human or non-human animal. In addition the compounds of formula (I) can be used for prophylaxis (preventative treatment). Treatment may include curative, alleviation or reducing effects, such effects relating to one or more of the symptoms associated with the central and peripheral nervous system-associated disorders.

One particular embodiment of the invention that can be mentioned is a compound of formula (I), particularly 5-[3-(2,5-dichloro-4,6-dimethyl-1-oxy-pyridin-3-yl)-[1,2,4]oxadiazol-5-yl]-3-nitrobenzene-1,2-diol and its pharmacologically acceptable salts, esters, carbamates and phosphates, for use in combination with a catecholamine drug, particularly levodopa, for the prophylaxis or treatment of central and peripheral nervous system disorder, particularly a movement disorder such as Parkinson's disease, wherein the compound of formula (I) is administered orally once daily at least one hour before or after the last daily dose of the catecholamine drug and prior to sleep, before bedtime or at bedtime and/or without food and/or between intakes of food and/or at least one hour after the most recent intake of food and at least one hour before the next intake of food.

According to another aspect of the present invention there is provided a method of treating at least one pathological state in a patient in need thereof comprising administering, without food and/or between intakes of food and/or prior to sleep and/or before bedtime and/or at bedtime and/or before or after administration of a catecholamine drug, a pharmacologically effective dose of a compound of general formula (I) as defined above to the patient.

According to another aspect of the invention there is provided a method for inhibiting COMT in a subject, comprising administering, without food and/or between intakes of food and/or prior to sleep and/or before bedtime and/or at bedtime and/or before or after administration of a catecholamine drug, an effective dose of a compound of general formula (I) as defined above to the subject.

According to another aspect of the invention there is provided a method for increasing levels of levodopa in the brain of a subject being treated with levodopa, comprising administering, without food and/or between intakes of food and/or prior to sleep and/or before bedtime and/or at bedtime and/or before or after administration of a catecholamine drug, an effective dose of a compound of general formula (I) as defined above to the subject.

According to another aspect of the invention there is provided a method for increasing levels of levodopa in the plasma of a subject being treated with levodopa, comprising administering, without food and/or between intakes of food and/or prior to sleep and/or before bedtime and/or at bedtime and/or before or after administration of a catecholamine drug, an effective dose of a compound of general formula (I) as defined above to the subject.

According to another aspect of the invention there is provided a method for decreasing levels of 3-O-methyl-levodopa (3-OMD) in the brain of a subject being treated with levodopa, comprising administering, without food and/or between intakes of food and/or prior to sleep and/or before bedtime and/or at bedtime and/or before or after administration of a catecholamine drug, an effective dose of a compound of general formula (I) as defined above to the subject.

According to another aspect of the invention there is provided a method for decreasing levels of 3-OMD in the plasma of a subject being treated with levodopa, comprising administering, without food and/or between intakes of food and/or prior to sleep and/or before bedtime and/or at bedtime and/or before or after administration of a catecholamine drug, an effective dose of a compound of general formula (I) as defined above to the subject.

According to another aspect of the invention there is provided a method for increasing bioavailability of levodopa in the brain of a subject being treated with levodopa, comprising administering, without food and/or between intakes of food and/or prior to sleep and/or before bedtime and/or at bedtime and/or before or after administration of a catecholamine drug, an effective dose of a compound of general formula (I) as defined above to the subject.

According to another aspect of the invention there is provided a method for increasing bioavailability of levodopa in the plasma of a subject being treated with levodopa, comprising administering, without food and/or between intakes of food and/or prior to sleep and/or before bedtime and/or at bedtime and/or before or after administration of a catecholamine drug, an effective dose of a compound of general formula (I) as defined above to the subject.

The present invention also relates to a package comprising a pharmaceutical composition of a compound of the general formula (I) in combination with instructions to administer said formulation without food and/or between intakes of food and/or prior to sleep and/or before bedtime and/or at bedtime and/or before or after administration of a catecholamine drug.

For the compounds of formula (I), the following definitions are preferred.

Groups hydrolysable under physiological conditions represent groups cleavable in vivo, at physiological conditions of pH and temperature. On page 1354 of the $6^{th}$ edition of "Foye's Principles of Medicinal Chemistry", 2006, eds. Wolter Kluwer, the pH values for tissue fluids are indicated. Examples of groups hydrolysable under physiological conditions for the —OH functional group are esters, carbamates and phosphates. Further examples of groups hydrolysable under physiological conditions for the —OH functional group are well known to the skilled in the art and can be found for example on pages 101-103 from Korolkovas in Essentials of Medicinal Chemistry, $2^{nd}$ edn., 1988, eds. John Wiley & Sons and on page 426 of Krogsgaard-larsen et al in Textbook of Drug Design and Discovery, $3^{rd}$ edn., 2002, eds. Taylor & Francis.

Preferably, $R_4$, $R_5$, $R_6$ and $R_7$ independently from each other represent hydrogen, $C_1$-$C_6$-alkyl, $C_6$-$C_{12}$ aryl, $C_1$-$C_6$-thioalkyl, $C_1$-$C_6$-alkoxy, $C_6$-$C_{10}$-aryloxy, $C_6$-$C_{10}$-thioaryl, $C_1$-$C_6$-alkanoyl, $C_7$-$C_{11}$-aroyl, amino, $C_1$-$C_6$-alkylamino, di-$C_1$-$C_6$-alkylamino, $C_3$-$C_{12}$-cycloalkylamino, $C_4$-$C_8$-heterocycloalkylamino, $C_1$-$C_6$-alkylsulphonyl, $C_6$-$C_{10}$-arylsulphonyl, halogen, $C_1$-$C_6$-haloalkyl, trifluoromethyl, cyano, nitro or heteroaryl.

When $R_4$, $R_5$, $R_6$ and/or $R_7$ represent $C_1$-$C_6$-alkyl residues, preferably $R_4$, $R_5$, $R_6$ and/or $R_7$ represent methyl, ethyl, n-propyl, isopropyl, n-butyl, sec-butyl, tert-butyl, pentyl, or hexyl.

When $R_4$, $R_5$, $R_6$ and/or $R_7$ represent $C_6$-$C_{12}$-aryl residues, preferably $R_4$, $R_5$, $R_6$ and/or $R_7$ represent phenyl or naphthyl.

When $R_4$, $R_5$, $R_6$ and/or $R_7$ represent $C_1$-$C_6$-thioalkyl residues, preferably $R_4$, $R_5$, $R_6$ and/or $R_7$ represent thiomethyl, thioethyl, thio-n-propyl, thio-isopropyl, thio-n-butyl, thio-n-pentyl, or thio-n-hexyl.

When $R_4$, $R_5$, $R_6$ and/or $R_7$ represent $C_1$-$C_6$-alkoxy residues, preferably $R_4$, $R_5$, $R_6$ and/or $R_7$ represent methoxy, ethoxy, n-propoxy, isopropoxy, n-butoxy, sec-butoxy or tert-butoxy.

When $R_4$, $R_5$, $R_6$ and/or $R_7$ represent $C_6$-$C_{10}$-aryloxy residues, preferably $R_4$, $R_5$, $R_6$ and/or $R_7$ represent phenoxy or naphthoxy.

When $R_4$, $R_5$, $R_6$ and/or $R_7$ represent $C_6$-$C_{10}$-thioaryl residues, preferably $R_4$, $R_5$, $R_6$ and/or $R_7$ represent thiophenyl or thionaphthyl.

When $R_4$, $R_5$, $R_6$ and/or $R_7$ represent $C_1$-$C_6$-alkanoyl residues, preferably $R_4$, $R_5$, $R_6$ and/or $R_7$ represent methanoyl, ethanoyl, propanoyl or butanoyl.

When $R_4$, $R_5$, $R_6$ and/or $R_7$ represent $C_7$-$C_{11}$-aroyl residues, preferably $R_4$, $R_5$, $R_6$ and/or $R_7$ represent benzoyl or naphthoyl.

When $R_4$, $R_5$, $R_6$ and/or $R_7$ represent $C_1$-$C_6$-alkylamino residues, preferably $R_4$, $R_5$, $R_6$ and/or $R_7$ represent methylamino, ethylamino, n-propylamino, isopropylamino or n-butylamino.

When $R_4$, $R_5$, $R_6$ and/or $R_7$ represent di-$C_1$-$C_6$-alkylamino residues, preferably $R_4$, $R_5$, $R_6$ and/or $R_7$ represent dimethylamino, diethylamino, di-n-propylamino, di-n-butylamino, di-isopropylamino, methylethylamino, methylpropylamino or ethylpropylamino.

When $R_4$, $R_5$, $R_6$ and/or $R_7$ represent $C_3$-$C_{12}$-cycloalkylamino residues, preferably $R_4$, $R_5$, $R_6$ and/or $R_7$ represent pyrrolidino, piperidino, cyclohexylamino or dicyclohexylamino.

When $R_4$, $R_5$, $R_6$ and/or $R_7$ represent $C_4$-$C_8$-heterocycloalkylamino residues, preferably $R_4$, $R_5$, $R_6$ and/or $R_7$ represent morpholino, 2,6-dimethylmorpholino, 3,5-dimethylmorpholino, piperazino, N-methylpiperazino or N-ethylpiperazino.

When $R_4$, $R_5$, $R_6$ and/or $R_7$ represent $C_1$-$C_6$-alkylsulphonyl or $C_6$-$C_{10}$-arylsulphonyl residues, preferably $R_4$, $R_5$, $R_6$ and/or $R_7$ represent methylsulfonyl, ethylsulfonyl, phenylsulfonyl, or tolylsulfonyl.

When $R_4$, $R_5$, $R_6$ and/or $R_7$ represent halogen residues, preferably $R_4$, $R_5$, $R_6$ and/or $R_7$ represent chloro, bromo, iodo or fluoro.

When $R_4$, $R_5$, $R_6$ and/or $R_7$ represent $C_1$-$C_6$-haloalkyl residues, preferably $R_4$, $R_5$, $R_6$ and/or $R_7$ represent chloromethyl, fluoromethyl, dichloromethyl, difluoromethyl, trichloromethyl or trifluoromethyl.

When $R_4$, $R_5$, $R_6$ and/or $R_7$ represent heteroaryl residues, preferably $R_4$, $R_5$, $R_6$ and/or $R_7$ represent pyridyl, pyrimidyl, isoxazolyl, oxazolyl, isoxadiazolyl, oxadiazolyl, triazolyl or tetrazolyl.

When two or more of residues $R_4$, $R_5$, $R_6$ and $R_7$ taken together represent aliphatic or heteroaliphatic rings or aromatic or heteroaromatic rings, the two or more residues preferably represent aliphatic or heteroaliphatic rings or aromatic or heteroaromatic rings. Preferred combined residues are indolizinyl, isoindolyl, indolyl, indazolyl, purinyl, quinolizinyl, naphthyridinyl, isoquinolyl and quinolyl.

Where they represent aryl or alkyl, the above substituents $R_4$, $R_5$, $R_6$ and $R_7$ may optionally be substituted one or more times by hydroxy, alkoxy or halogen groups.

In the present description of medical indications, treatments and dosing regimens for pharmaceutical compositions containing compounds according to general formula (I) of the invention, the most preferred example of a compound according to the general formula (I) is 5-[3-(2,5-dichloro-4,6-dimethyl-1-oxy-pyridin-3-yl)-[1,2,4]oxadiazol-5-yl]-3-nitrobenzene-1,2-diol, henceforth designated as compound A, and its pharmacologically acceptable salts, esters, carbamates and phosphates. The half life of compound A is relatively short given its long duration of action.

Other preferred compounds of the above general formula (I) for use in the subsequent medical indications, treatments and dosing regimens include 3-(3-(3,4-dihydroxy-5-nitrophenyl)-1,2,4-oxadiazol-5-yl)-4-(trifluoromethyl)pyridine-1-oxide, 2-chloro-3-(3-(3,4-dihydroxy-5-nitrophenyl)-1,2,4-oxadiazol-5-yl)-4,6-dimethylpyridine-1-oxide, 3-(3-(3,4-dihydroxy-5-nitrophenyl)-1,2,4-oxadiazol-5-yl)-2-methyl-6-(trifluoromethyl)pyridine-1-oxide, 5-(3-(3,4-dihydroxy-5-nitrophenyl)-1,2,4-oxadiazol-5-yl)-2-(trifluoromethyl) pyridine-1-oxide, 5-(3-(3,4-dihydroxy-5-nitrophenyl)-1,2,4-oxadiazol-5-yl)-2-methyl-4-(trifluoromethyl)pyridine-1-oxide, 3-(3-(3,4-dihydroxy-5-nitrophenyl)-1,2,4-oxadiazol-5-yl)-2,6-dimethyl-4-(trifluoromethyl)pyridine-1-oxide, 3,5-dichloro-4-(3-(3,4-dihydroxy-5-nitrophenyl)-1,2,4-oxadiazol-5-yl)pyridine-1-oxide, 3-(3-(3,4-dihydroxy-5-nitrophenyl)-1,2,4-oxadiazol-5-yl)-6-methyl-2-phenyl-4-(trifluoromethyl)pyridine-1-oxide, 2-bromo-3-(3-(3,4-dihydroxy-5-nitrophenyl)-1,2,4-oxadiazol-5-yl)-4,5,6-trimethylpyridine-1-oxide, 2-chloro-3-(3-(3,4-dihydroxy-5-nitrophenyl)-1,2,4-oxadiazol-5-yl)-4,5,6-trimethylpyridine-1-oxide, 3-(3-(3,4-dihydroxy-5-nitrophenyl)-1,2,4-oxadiazol-5-yl)-2-(trifluoromethyl)pyridine-1-oxide, 2,5-dichloro-3-(3-(3,4-dihydroxy-5-nitrophenyl)-1,2,4-oxadiazol-5-yl)-4,6-dimethylpyridine-1-oxide, 3-(3-(3,4-dihydroxy-5-nitrophenyl)-1,2,4-oxadiazol-5-yl)-5-(trifluoromethyl)pyridine-1-oxide, 3-(3-(3,4-dihydroxy-5-nitrophenyl)-1,2,4-oxadiazol-5-yl)-2-fluoropyridine-1-oxide, 4-(3-(3,4-dihydroxy-5-nitrophenyl)-1,2,4-oxadiazol-5-yl)-2-fluoropyridine-1-oxide, 2-(3-(3,4-dihydroxy-5-nitrophenyl)-1,2,4-oxadiazol-5-yl)-6-fluoropyridine-1-oxide, 2-chloro-3-(3-(3,4-dihydroxy-5-nitrophenyl)-1,2,4-oxadiazol-5-yl)-6-methylpyridine 1-oxide, 2-bromo-3-(3-(3, 4-dihydroxy-5-nitrophenyl)-1,2,4-oxadiazol-5-yl)-6-methylpyridine-1-oxide, and 2-bromo-5-chloro-3-(3-(3,4-dihydroxy-5-nitrophenyl)-1,2,4-oxadiazol-5-yl)-4,6-dimethylpyridine-1-oxide and their pharmacologically acceptable salts, esters, carbamates or phosphates.

Details of the preparation of compounds of general formula (I) can be found in WO2007/013830A1.

The compounds of general formula (I) may also be present in the form of pharmacologically acceptable salts, esters, carbamates or phosphates thereof. Suitable pharmaceutically acceptable counter ions are known to the art.

It is also possible to use prodrugs of compounds of the general formula (I) in order to alter the therapeutic profile of the active compound.

The compound of formula (I) is administered as a pharmaceutical composition. For the preparation of pharmaceutical compositions of compounds of general formula I, inert pharmaceutically acceptable carriers are admixed with the active compounds. The pharmaceutically acceptable carriers may be solid or liquid. Solid form preparations include powders, tablets, dispersible granules and capsules. A solid carrier can be one or more substances which may also act as diluent, flavouring agent, solubiliser, lubricant, suspending agent, binder, glidant, or disintegrant; it may also be an encapsulating material.

Preferably the pharmaceutical composition is in unit dosage form, e.g. a packaged preparation, the package containing discrete quantities of the preparation, for example packaged tablets, capsules and powders in vials or ampoules.

In general, the compound of formula (I) is administered orally.

The compound of formula (I) typically is administered from once a day to about once weekly.

For the avoidance of doubt, whenever the compound of formula (I) is administered with a periodicity lower than once a day (e.g. once weekly), it is understood that it will be administered prior to sleep, before bedtime or at bedtime, before or after the last daily dose of levodopa of the day(s) of the week where compound (I) should be administered and not every day, as levodopa. For example, for a once weekly administration regime, if compound (I) is administered on the first day of week one, it will be administered prior to sleep, before bedtime or at bedtime, before or after the last daily dose of levodopa of that day. The next administration will occur on the first day of week two, prior to sleep, before bedtime or at bedtime, before or after the last daily dose of levodopa of that day and so on. Throughout this period levodopa is administered every day (in several doses).

According to the methods described above, the compound of formula (I) is typically administered from once a day to about once weekly.

Other aspects of the invention are as defined in the claims.

EXAMPLES

Example 1: Preparation of Compound A (5-[3-(2,5-Dichloro-4,6-dimethyl-1-oxy-pyridin-3-yl)-[1,2,4]oxadiazol-5-yl]-3-nitrobenzene-1,2-diol)

a) To a stirred solution of 3,4-dibenzyloxy-5-nitrobenzoic acid (0.50 g, 1.319 mmol) in dimethylformamide (5 mL) at room temperature was added 1,1-carbonyldiimidazole (0.24 g, 1.45 mmol) in one portion. After stirring for ninety minutes, 2,5-dichloro-N'-hydroxy-4,6-dimethylnicotinamide (0.40 g, 1.45 mmol) was added in one portion. The resulting mixture was stirred at 135° C. for five hours and then at room temperature overnight. The reaction mixture was poured onto ice-2 N HCl (100 mL) and the resulting precipitate was filtered off, washed with water and dried in air. Recrystallisation from isopropanol gave a pale yellow solid (0.55 g, 72%).

b) To a stirred solution of the solid obtained above (0.50 g, 0.866 mmol) in dichloromethane (20 mL) was added urea-hydrogen peroxide addition complex (0.41 g, 4.33 mmol) in one portion. The mixture was cooled in an ice-water bath and trifluoroacetic anhydride (0.73 g, 3.46 mmol) was added dropwise. The reaction mixture was allowed to stir at room temperature overnight whereupon insoluble material was filtered off. The filtrate was washed with water and brine, dried over anhydrous magnesium sulphate, filtered and evaporated. The residue was crystallised from isopropanol to give a pale yellow solid (0.35 g, 68%).

c) To a stirred solution of the solid obtained above (0.30 g, 0.5 mmol) in dichloromethane (10 mL) at −78° C. under argon was added boron tribromide (0.38 g, 1.5 mmol) dropwise. The resulting purple suspension was allowed to stir at room temperature for one hour, then cooled again to −78° C. and carefully quenched by the addition of water. After stirring at room temperature for one hour, the precipitate was filtered off, washed with water and dried at 50° C. under vacuum to afford the desired compound as yellow crystals (0.18 g, 87%) of m.p. 237-240° C.

Example 2: Pharmaceutical Formulation

Pharmaceutical formulations are prepared as follows:

Capsule:

| | |
|---|---|
| Compound A | 15.0% |
| Lactose monohydrate | 43.0% |
| Microcrystalline cellulose | 30.0% |
| Povidone | 4.0% |
| Croscarmellose sodium | 5.0% |
| Talc | 2.0% |
| Magnesium stearate | 1.0% |

Capsule:

| | |
|---|---|
| Compound A | 15.0% |
| Microcrystalline cellulose | 72.5% |
| Ethylcellulose | 5.0% |
| Sodium starch glycolate | 6.0% |
| Colloidal Silicon Dioxide | 0.5% |
| Magnesium stearate | 1.0% |

Tablet:

| | |
|---|---|
| Compound A | 20.0% |
| Microcrystalline cellulose | 25.0% |
| Calcium Phosphate, dibasic dihydrate | 40.0% |
| Povidone | 6.0% |
| Croscarmellose sodium | 6.0% |
| Talc | 2.0% |
| Magnesium stearate | 1.0% |

Example 3—Dosing Regimen

Example 3a: Effect of Food

This study was an open-label, randomized, single administration, 2-period, 2-sequence, crossover study in 12 healthy male subjects aimed to assess the effects of food on the pharmacokinetic (PK) profile of COMPOUND A and its metabolites. A single 50 mg dose of COMPOUND A (2×25 mg capsules) was administered under fasted and fed conditions.

Blood samples were collected prior to and 0.5, 1, 1.5, 2, 3, 4, 6, 8, 10, 12, 16 and 24 hours after administration of COMPOUND A.

Figure 1:
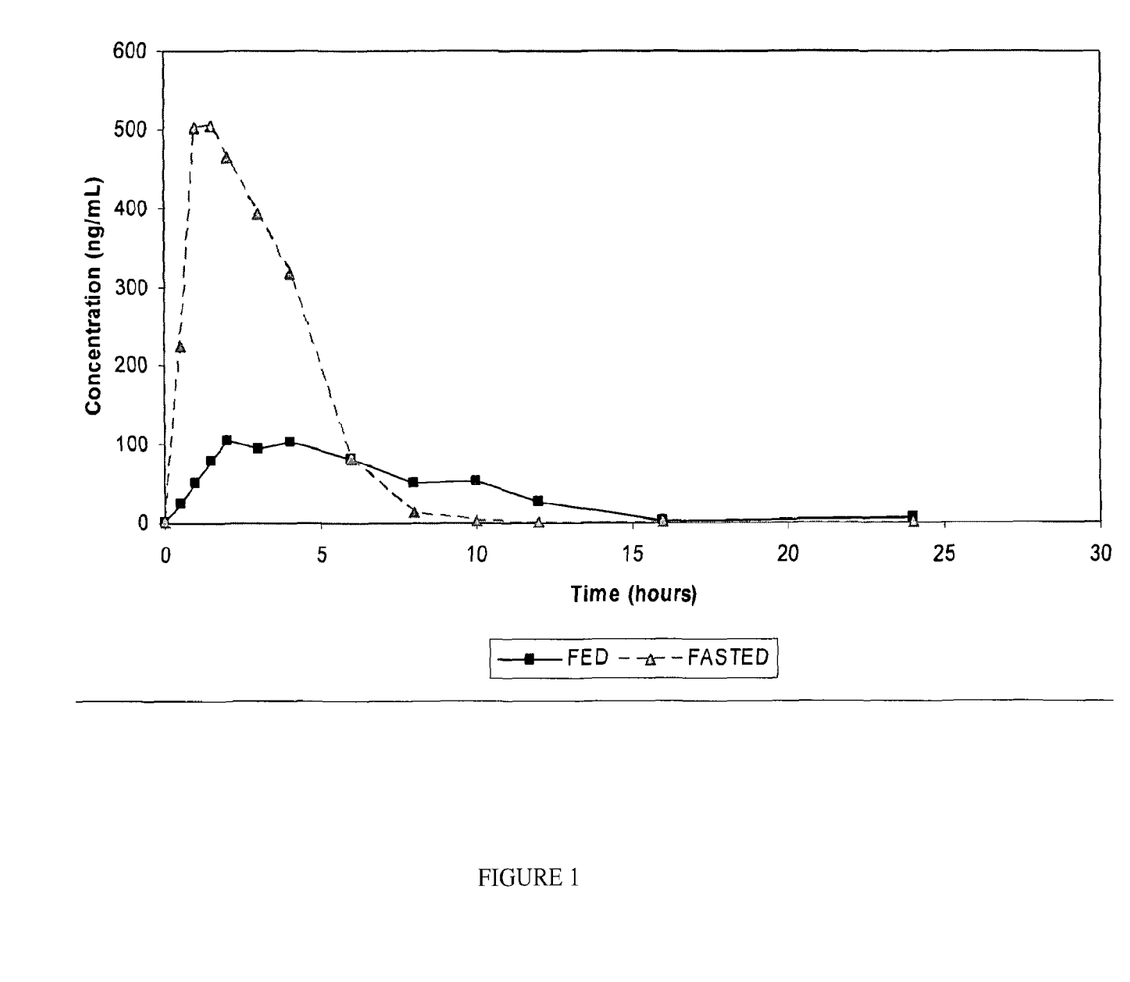
FIG. 1 shows mean plasma concentration-time profile of 5-[3-(2,5-dichloro-4,6-dimethyl-1-oxy-pyridin-3-yl)-[1,2,4]oxadiazol-5-yl]-3-nitrobenzene-1,2-diol (COMPOUND A) following fasting and fed conditions.

Pharmacokinetic Results:

Following an oral single dose of 50 mg (2×25 mg capsules), the bioavailability of COMPOUND A was not equivalent under fasting and fed conditions, indicating the presence of a food effect on COMPOUND A pharmacokinetics (FIG. 1).

The COMPOUND A pharmacokinetic parameters following fasting and fed conditions are presented in Table 1. Summary of PK main results of COMPOUND A following fasting and fed conditions.

TABLE 1

Summary of PK main results of COMPOUND
A following fasting and fed conditions.

| PARAMETER | Fed | | Fasted | | F (treatment) | p* |
|---|---|---|---|---|---|---|
| | MEAN | C.V. (%) | MEAN | C.V. (%) | | |
| $C_{max}$ (ng/mL) | 238.2 | 70.7 | 635.0 | 39.5 | 24.84 | <0.01 |
| ln ($C_{max}$) | 5.2927 | 11.4 | 6.3868 | 5.9 | 41.50 | <0.001 |
| $T_{max}$ (hours)§ | 4.00 | 66.3 | 1.50 | 62.9 | 18 | <0.05 |
| $AUC_T$ (ng · h/mL) | 879.2 | 32.6 | 1989.5 | 49.5 | 15.95 | <0.01 |
| ln ($AUC_T$) | 6.7286 | 5.1 | 7.4900 | 6.4 | 34.22 | <0.001 |
| $AUC_\infty$ (ng · h/mL) | 1027.2 | 53.1 | 2113.6 | 43.3 | 36.53 | <0.001 |
| ln ($AUC_\infty$) | 6.8416 | 6.2 | 7.5771 | 5.5 | 52.24 | <0.001 |
| $AUC_{T/\infty}$ (%) | 90.06 | 12.1 | 93.49 | 17.0 | 0.75 | N.S. |
| $K_{el}$ (hours$^{-1}$) | 0.4021 | 46.0 | 0.7581 | 38.9 | 15.99 | <0.01 |
| $T_{1/2el}$ (hours) | 3.35 | 141.2 | 1.19 | 80.5 | 2.19 | N.S. |

*N.S. = Not Significant. Significant whenever p-value < 0.05;
§For $T_{max}$, the median is presented and the statistical analysis is based on a non-parametric approach.
C.V.—Coefficient of Variation The ingestion of food decreased and delayed the absorption of COMPOUND A; the administration of COMPOUND A immediately following consumption of a high-fat, high-calorie meal significantly decreased the rate and extent of absorption compared to drug administration under fasting conditions. $C_{max}$ and AUC parameters were significantly lower in the fed state compared to the fasted state (fed:fasted ratios of 31.73% for $C_{max}$, 47.11% for $AUC_T$ and 49.43% for $AUC_\infty$). The $T_{max}$ was significantly increased by the presence of food (4.00 hours in the fed state versus 1.50 hours in the fasted state).

Conclusions:

The results show that the administration of COMPOUND A following food intake results in a reduction in its bioavailability. The presence of food decreased the rate and extent of absorption of COMPOUND A, with delayed peak plasma levels as compared to drug administration under fasting conditions.

Example 3b: Administration of Levodopa and Compound A Concomitantly and Separated by 1 Hour This study was a single-centre, open-label, randomized, gender-balanced, crossover study with four consecutive single-administration treatment periods to assess the PK-PD interaction when standard release 25/100 mg carbidopa/levodopa is administered concomitantly with a 50 mg COMPOUND A dose or 1 hour thereafter. Eighteen (18) subjects completed 2 treatment periods, 17 subjects completed 3 treatment periods and 16 subjects completed all 4 treatment periods. A total of 18 male [10 (55.6%)] and female [8 (44.4%)] subjects were enrolled in this study.

Treatment consisted of four single-administration periods. Single-administration of 50 mg COMPOUND A was constituted by 2 capsules of 25 mg. Single-administration of immediate/standard release 25 mg carbidopa/100 mg levodopa was constituted of 1 tablet of Sinemet® 100/25. In accordance to the treatment sequence defined by the randomization, subjects were administered COMPOUND A and Sinemet® 100/25 concomitantly in one period, Sinemet® 100/25 1 h after the COMPOUND A administration in another period, COMPOUND A alone in another period, and Sinemet® 100/25 alone in the remaining period. The washout period between administrations was at least 3 weeks. In one treatment period, COMPOUND A and Sinemet® 100/25 were to be administered concomitantly; in another treatment period, Sinemet® 100/25 was to be administered 1 h after the COMPOUND A administration; in another treatment period, COMPOUND A was to be administered alone; in the remaining treatment period, Sinemet® 100/25 was to be administered alone.

Mean levodopa $C_{max}$ values were attained between 0.5 to 1.0 hours post-administration. Thereafter, plasma levodopa concentrations declined with a mean elimination half-life (t1/2) ranging from 1.94 (Sinemet® 100/25 alone) to 2.51 (Sinemet® 100/25 plus 50 mg COMPOUND A concomitantly) hours.

Following administration with COMPOUND A, the levodopa $C_{max}$ increased and the increase was higher when COMPOUND A was administered concomitantly, suggesting that a certain degree of interaction between COMPOUND A and Sinemet® 100/25 may have occurred during the absorption phase, leading to an increase in the rate of levodopa uptake and a less smooth increase in levodopa levels.

Figure 2:
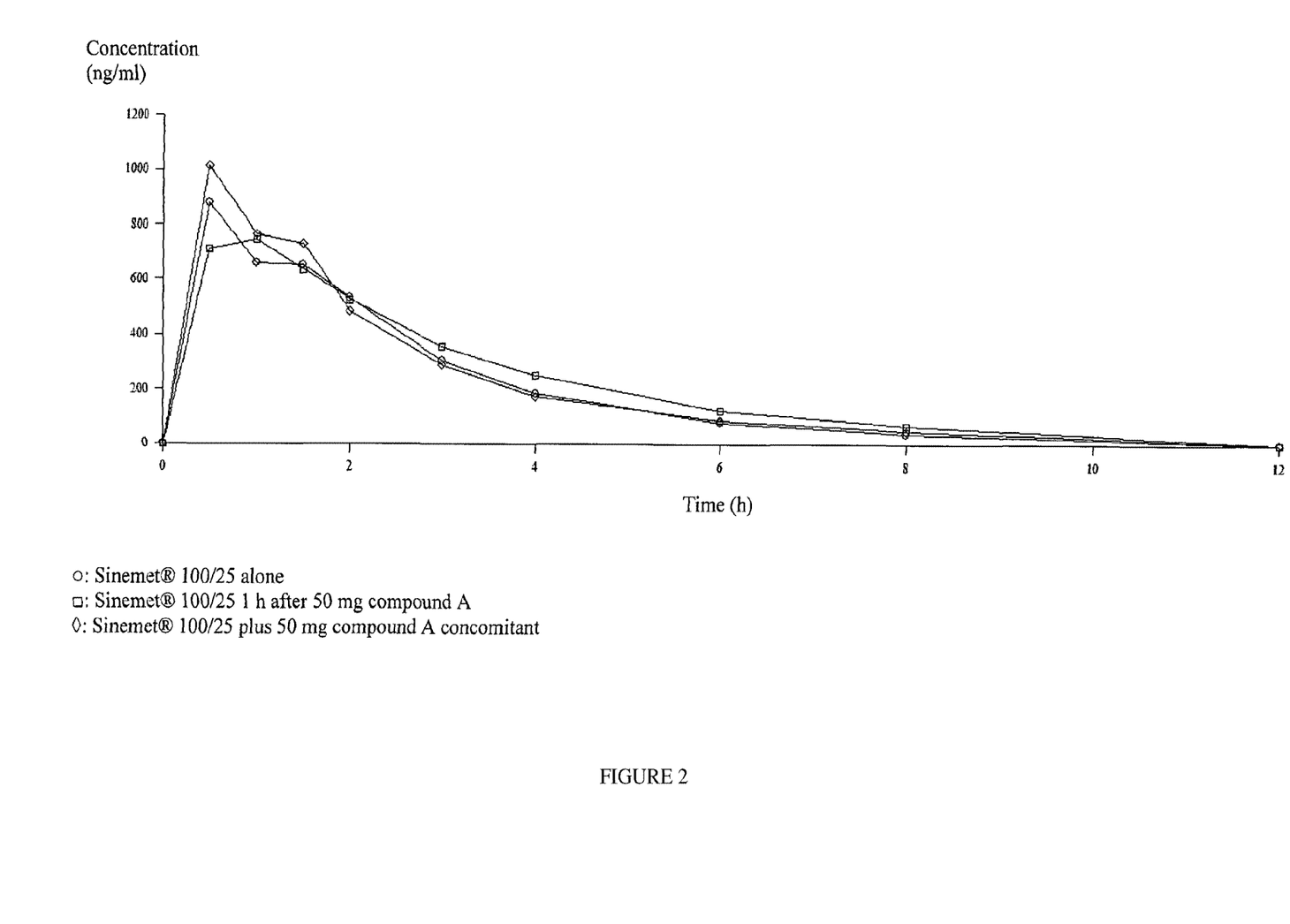
FIG. 2 shows mean levodopa plasma concentration-time profiles following single oral administration of Sinemet® (levodopa/carbidopa) 100/25 mg administered alone, administered with 50 mg COMPOUND A separated 1 h and administered concomitantly with 50 mg COMPOUND A.

Mean levodopa plasma concentration-time profiles following single oral administration of Sinemet® 100/25 administered alone, administered with 50 mg COMPOUND A separated 1 h and administered concomitantly with 50 mg COMPOUND A are illustrated in FIG. 2 (n=16 for concomitant administration, n=17 for Sinemet® alone, n=18 for administration separated 1 h):

The Point Estimates and 90% Confidence Interval of the mean pharmacokinetic parameters of levodopa following 50 mg COMPOUND A concomitant administration (Test L1) and an administration separated 1 h (Test L2) with Sinemet® 100/25 are displayed in Table 2 (Sinemet® 100/25 alone was taken as Reference):

TABLE 2

Point estimates and 90% CI of the mean pharmacokinetic parameters of levopoda following 50 mg COMPOUND A concominant administration (Test L1) and an administration seperated 1 h (Test L2) with Sinemet ® 100/25

| Comparison | $C_{max}$ PE (90% CI) | $AUC_{0-t}$ PE (90% CI) | $AUC_{0-\infty}$ PE (90% CI) |
|---|---|---|---|
| Test L1/Reference L | 112.10 (96.94; 129.64) | 104.23 (96.88; 112.14) | 103.13 (94.02; 113.12) |
| Test L2/Reference L | 102.96 (89.36; 118.62) | 114.56 (106.65; 123.05) | 109.85 (100.22; 120.41) |
| Test L2/Test L1 | 91.84 (79.51; 106.09) | 109.91 (102.17; 118.24) | 108.51 (101.24; 116.31) |

PE = Point estimate;
CI = Confidence interval

A greater increase in the extent of exposure to levodopa (as assessed by AUC) occurred when Sinemet® 100/25 was administered 1 h after 50 mg COMPOUND A.

The increase in levodopa $AUC_{0-t}$ ranged from 4.23% when Sinemet® 100/25 was administered concomitantly with 50 mg COMPOUND A (ratios=104.23 [96.88; 112.14]; means and 90% CIs) to 14.56% when Sinemet® 100/25 was administered 1 h after 50 mg COMPOUND A (ratios=114.56 [106.65; 123.05]). The increase in levodopa $AUC_{0-\infty}$ ranged from 3.13% when Sinemet® 100/25 was administered concomitantly with 50 mg COMPOUND A (ratios=103.13 [94.02; 113.12]) to 9.85% when Sinemet® 100/25 was administered 1 h after 50 mg COMPOUND A (ratios=109.85 [100.22; 120.41]).

The increase in levodopa $C_{max}$ ranged from 2.96% when Sinemet® 100/25 was administered 1 h after 50 mg COMPOUND A (ratios=102.96 [89.36; 118.62]) to 12.10% when Sinemet® 100/25 was administered concomitantly with 50 mg COMPOUND A (ratios=112.10 [96.94; 129.64]), showing a preferred steadier increase in levodopa levels with administration of Sinemet® 100/25 was administered 1 h after COMPOUND A.

$C_{max}$ of 3-OMD was lower when Sinemet® 100/25 was administered 1 h after 50 mg COMPOUND A than when Sinemet® 100/25 was administered concomitantly with 50 mg COMPOUND A. A significant decrease in both rate (as assessed by $C_{max}$) and extent (as assessed by AUC) of systemic exposure to 3-OMD occurred when Sinemet® 100/25 was administered concomitantly and also 1 h after 50 mg COMPOUND A.

$C_{max}$ and AUC of carbidopa were similar when Sinemet® 100/25 was administered alone and when administered with 50 mg COMPOUND A separated 1 h. The increase in carbidopa $C_{max}$ ranged from 5.33% when Sinemet® 100/25 was administered 1 h after 50 mg COMPOUND A to 5.86% when Sinemet® 100/25 was administered concomitantly with 50 mg COMPOUND A. The increase in carbidopa $AUC_{0-\infty}$ ranged from 5.42% when Sinemet® 100/25 was administered 1 h after 50 mg COMPOUND A to 9.20% when Sinemet® 100/25 was administered concomitantly with 50 mg COMPOUND A.

Mean COMPOUND A $C_{max}$ values were attained between 2.5 to 4.0 hours post-administration. Thereafter, plasma COMPOUND A concentrations declined with a mean elimination half-life (t1/2) ranging from 1.14 (COMPOUND A alone) to 1.28 (COMPOUND A with Sinemet® 100/25) hours. $C_{max}$ of COMPOUND A was lower when COMPOUND A was administered 1 h before Sinemet® 100/25 than when was administered concomitantly with Sinemet® 100/25 and even lower in relation to when COMPOUND A was administered alone. Following administration with Sinemet® 100/25, the COMPOUND A $C_{max}$ decreased and $t_{max}$ increased, suggesting that a certain degree of interaction between COMPOUND A and Sinemet® 100/25 may have occurred during the absorption phase, leading to a delay in the rate of COMPOUND A uptake. A statistical difference was found for $t_{max}$ between 50 mg COMPOUND A administered concomitantly with Sinemet® 100/25 and COMPOUND A administered alone (p=0.0020). The increase in COMPOUND A $AUC_{0-\infty}$ ranged from 4.18% when Sinemet® 100/25 was administered concomitantly with 50 mg COMPOUND A to 4.74% when Sinemet® 100/25 was administered 1 h after 50 mg COMPOUND A. There was a decrease in COMPOUND A $C_{max}$ of 9.21% when Sinemet® 100/25 was administered 1 h after 50 mg COMPOUND A.

Figure 3:
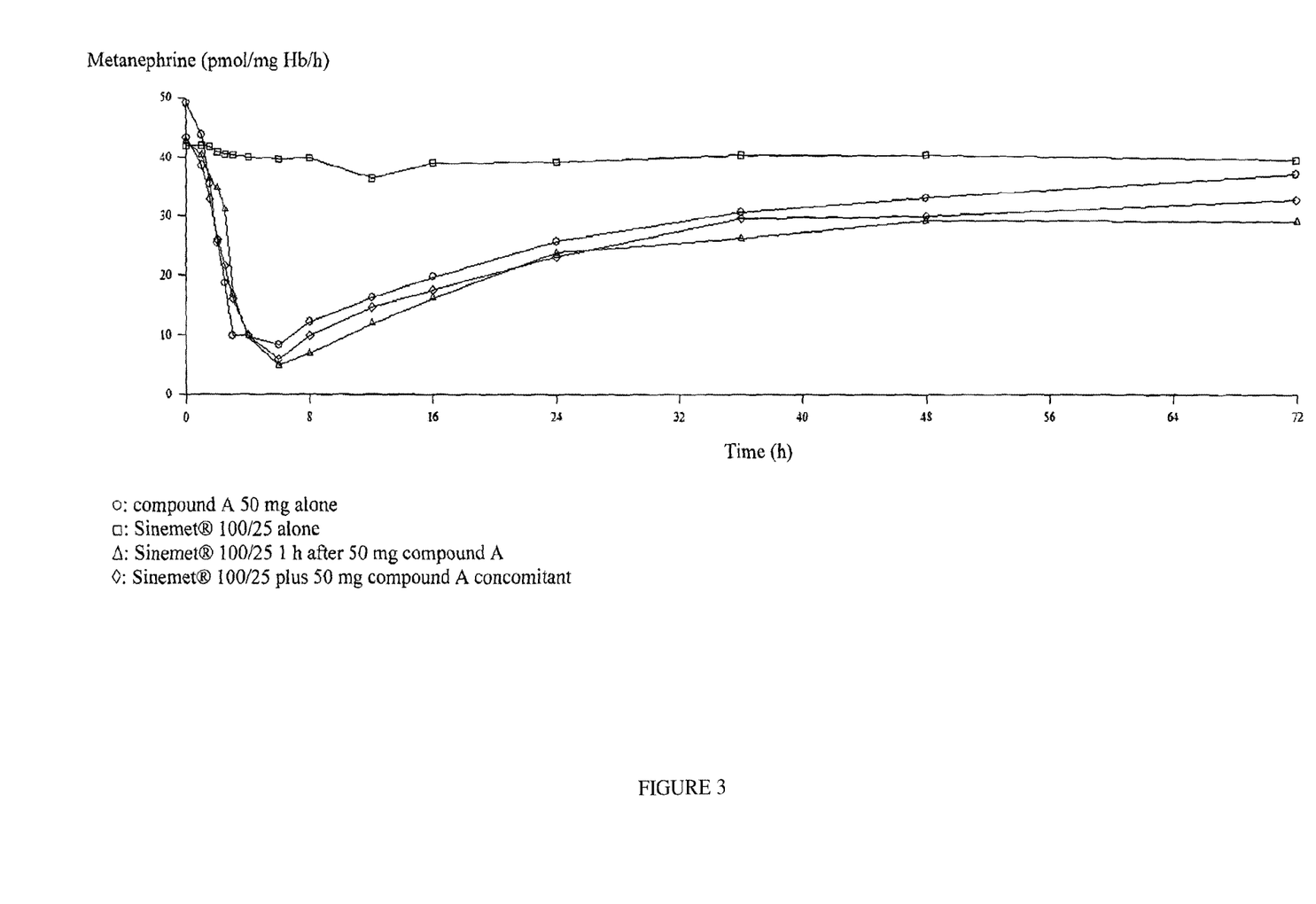
FIG. 3 shows mean S-COMT activity (metanephrine formed, pmol/mg protein/h) profiles from baseline (pre-dose) following single oral administration of Sinemet® 100/25 administered alone, administered with 50 mg COMPOUND A separated 1 h, administered concomitantly with 50 mg COMPOUND A and when COMPOUND A was administered alone.

Pharmacodynamic Results:

Mean S-COMT activity (metanephrine formed, pmol/mg protein/h) profiles from baseline (pre-administration) following single oral administration of Sinemet® 100/25 administered alone, administered with 50 mg COMPOUND A separated by 1 h, administered concomitantly with 50 mg COMPOUND A and when COMPOUND A was administered alone were as follows (FIG. 3) (n=16 for concomitant administration, n=17 for Sinemet® alone, n=18 for COMPOUND A alone and for administration separated by 1 h):

All COMPOUND A treatments significantly inhibited both peak and extent of S-COMT activity in relation to Sinemet® 100/25 alone administration. Following administration of COMPOUND A, maximum S-COMT inhibition ($E_{max}$) occurred between 3.42 h (COMPOUND A alone) and 4.58 h (Sinemet® 100/25 administered 1 h after 50 mg COMPOUND A) post-administration ($tE_{max}$), and ranged from 88.7% to 91.1%, respectively.

Conclusions:

The results were highly consistent across the multiple analyses performed. All COMPOUND A treatments significantly inhibited both peak and extent of S-COMT activity in relation to Sinemet® 100/25 alone administration. The concomitant administration of COMPOUND A with Sinemet® 100/25 showed an effect on both levodopa and COMPOUND A absorption. In the latter, as well as the slight $C_{max}$ decrease, a significant increase in COMPOUND A $t_{max}$ was observed. With respect to levodopa, delaying by 1 hour the administration with COMPOUND A, a $C_{max}$ decrease (when compared to the increase observed with the concomitant administration) was seen, suggesting that the possible interaction between COMPOUND A and Sinemet® 100/25 during the absorption phase was reduced by separating both administrations. Furthermore, delaying by 1 hour the administration of levodopa with COMPOUND A, an increase in levodopa systemic exposure (as assessed by AUC) was observed. This could be attributed to the absorption rate of COMPOUND A and consequently to the inhibition of COMT. Indeed, and despite the significant increase in the $tE_{max}$ for both treatments with COMPOUND A and Sinemet® 100/25 in relation to the administration of COMPOUND A alone, the 1 hour separated administration induced a more sustained absorption rate of COMPOUND A in contrast to the abrupt and delayed absorption observed with the concomitant administration. This may have resulted in an early inhibition of COMT and consequent increase in levodopa systemic exposure.

Example 3c: Effect of Compound A on Patient's Levodopa Exposure after Administration of L-DOPA and Compound A Concomitantly Followed by Further Administration of L-DOPA 24 h Later This study was a three-center, double-blind, randomised, placebo-controlled, cross-over study to investigate the tolerability and effect a single administration of three dosages of COMPOUND A (25, 50 and 100 mg) on the levodopa pharmacokinetics, motor response, and erythrocyte soluble catechol-O-methyltransferase activity in 10 Parkinson's Disease patients concomitantly treated with levodopa/dopadecarboxylase inhibitor.

Subjects were eligible if they presented: a diagnosis of PD according to the UK PDS Brain Bank diagnostic criteria; predictable signs of end-of-dose deterioration despite "optimal" levodopa/AADCi therapy; being treated with a stable regimen of 3 to 8 doses of standard release levodopa/AADCi 100/25 mg per day within at least 1 week prior to randomisation; modified Hoehn and Yahr stage of less than 5 in the off-state; and/or mean duration of OFF stage ≥1.5 h during waking hours. Concomitant anti-Parkinsonian medication (other than apomorphine, entacapone or tolcapone) was allowed in stable doses for at least 4 weeks prior to randomisation.

Manipulating the dose and frequency of levodopa administration is the common therapeutic approach to the onset of motor complications. This is usually described as optimization of levodopa therapy. "Optimal" levodopa/AADCi therapy is the levodopa/AADCi dosage and administration regime, which produces the best motor response in a patient, i.e. absence or reduction to a minimum of end-of-dose deterioration (wearing-off) and/or motor complications.

The study consisted of four consecutive treatment periods, corresponding to the 4 different treatment options (Compound A 25 mg, 50 mg, 100 mg or placebo). In each of the four treatment periods, subjects were to be admitted to the study site 2 days prior to receiving the administration of Compound A/Placebo (Day 1) and were to remain hospitalized ("in-patient") until 48 h after receiving the administration of Compound A/Placebo. The washout period between administrations was to be at least 10 days. A follow-up visit was to occur approximately 2 weeks after the last treatment administration or early discontinuation. During each period, the COMPOUND A/Placebo capsules were to be co-administered with the morning dose of levodopa/carbidopa 100/25 mg (1 tablet of Sinemet® 25/100) or levodopa/benserazide 100/25 mg (1 tablet of Madopar®/Restex® 125) on Day 3.

A total of 10 subjects were enrolled in this study: 10 subjects completed 3 treatment periods and 9 subjects completed all 4 treatment periods. The mean (±SD) age, height and weight were 58.40±10.24 (range: 42-70) years, 1.69±0.14 (1.52-1.95) m, 71.5±15.06 (50-100) kg, respectively.

Results from this study can be found in Table 3 and Table 4.

TABLE 3

Mean pharmacokinetic (PK) parameters of levodopa following single oral administration of Sinemet ® 25/100 or Madopar ®/Restex ® 125 on Day 2, Day 3 and Day 4.

| | Comparison | Treatment | $C_{max}$ (ng/mL) | $t_{max}$ (h) | $AUC_{0-6}$ (ng · h/mL) | $t_{1/2}$ (h) |
|---|---|---|---|---|---|---|
| Day 2 | Group 1 | — | 2513 | 0.5 | 4325 | 1.70 |
| 24 h before | Group 2 | — | 2237 | 0.5 | 4294 | 1.63 |
| administration of | Group 3 | — | 2086 | 0.5 | 3830 | 1.88 |
| Compound A | Group 4 | — | 1881 | 1.0 | 4141 | 1.78 |
| Day 3 | Group 1 | Placebo | 2103 | 0.5 | 3958 | 1.60 |
| concomitant | Group 2 | COMPOUND A - 25 mg | 2112 | 1.0 | 4545 | 1.97 |
| administration of Compound A | Group 3 | COMPOUND A - 50 mg | 2366 | 0.5 | 4580 | 1.77 |
| | Group 4 | COMPOUND A - 100 mg | 2657 | 0.5 | 5440 | 2.05 |
| Day 4 | Group 1 | — | 2128 | 0.5 | 3823 | 1.96 |
| 24 h after | Group 2 | — | 2369 | 0.5 | 4658 | 1.77 |
| administration of | Group 3 | — | 2583 | 0.5 | 5178 | 1.84 |
| Compound A | Group 4 | — | 2479 | 1.0 | 5697 | 2.08 |

TABLE 4

Point estimates (PE) and 90% CI of mean PK parameters of levodopa following single oral administration of Sinemet ® 25/100 or Madopar ®/Restex ® 125 and placebo, 25 mg, 50 mg and 100 mg COMPOUND A on Day 3 and Day 4.

| Comparison | $C_{max}$ PE (90% CI) | $AUC_{0-6}$ PE (90% CI) |
|---|---|---|
| Day 3 (concomitant administration of compound A) | | |
| Placebo - Day 3/Day 2 | 93.49 (62.23; 140.45) | 82.11 (55.90; 120.61) |
| COMPOUND A 25 mg - Day 3/Day 2 | 90.10 (60.66; 133.84) | 100.68 (66.58; 152.24) |
| COMPOUND A 50 mg - Day 3/Day 2 | 117.00 (78.87; 173.56) | 121.94 (88.57; 167.89) |
| COMPOUND A 100 mg - Day 3 Day 2 | 144.54 (104.41; 200.09)* | 133.18 (90.22; 196.60) |
| Day 4 (24 h after administration of compound A) | | |
| Placebo - Day 4/Day 2 | 83.26 (55.84; 124.16) | 93.45 (63.99; 136.48) |
| COMPOUND A 25 mg - Day 4/Day 2 | 109.18 (80.03; 148.94) | 110.54 (77.14; 158.40) |
| COMPOUND A 50 mg - Day 4/Day 2 | 128.79 (87.21; 190.19) | 138.79 (101.18; 190.38)* |
| COMPOUND A 100 mg - Day 4/Day 2 | 120.93 (79.59; 183.74) | 132.36 (86.56; 202.39) |

*significantly different.

Example 3d: Clinical Trial Inpatients with
Parkinson's Disease: Dosage Prior to Sleep In this study, the Compound A is tested as the research therapy and entacapone and placebo as the reference therapies. Compound A is available in capsules of 5 mg, 25 mg and 50 mg. Entacapone tablets of 200 mg are used. To ensure blinding during the Double Blind (DB) period, the Compound A capsules and entacapone tablets are identically over-encapsulated. The placebo capsules are prepared by filling identical capsules with filler (also used as backfilling). All placebo capsules contain, on average, 1 mg riboflavin to mimic the urinary discoloration seen as a harmless side effect of entacapone
Dosage Schedule
During the DB period, subjects take 1 capsule of treatment concomitantly with each daytime levodopa/AADCi administration (3 to 8 daily administrations). An additional treatment ('before bedtime' or 'prior to sleep' administration) is administered at least 1 hour after the last administration of the day of levodopa/AADCi.
For the daytime administrations (i.e. taken concomitantly with each levodopa/AADCi administration), the treatment administration is as follows:
 Compound A Groups: placebo.
 Entacapone Group: 200 mg entacapone.
 Placebo Group: placebo.
For the bedtime dose (at least 1 hour after the last daily administration of levodopa/AADCi), the treatment administration is as follows:
 Compound A Groups: 5, 25 or 50 mg.
 Entacapone Group: placebo.
 Placebo Group: placebo.

Example 3e: Clinical Trial in Patients with
Parkinson's Disease: Dosage Prior to Sleep and 1
Hour after Food Intake In a double blind, placebo controlled study, patients with Parkinson's disease maintained on levodopa/AADCi are treated as follows. Patients take either the placebo or compound A (25 mg or 50 mg) in the evening at least one hour after the last dose of the day of levodopa/AADCi therapy (the bedtime dose (administration)).

Subjects are required to fast for 1 hour before and for at least 1 hour after intake of the treatment.

Patients who take compound A are expected to show improved effects relative to those taking the placebo.

The invention claimed is:

1. A method of treating Parkinson's disease, comprising orally administering to a human patient suffering from said disease, without food and/or between intakes of food, a therapeutically effective amount of compound 5-[3-(2,5-dichloro-4,6-dimethyl-1-oxy-pyridin-3-yl)-[1,2,4]oxadiazol-5-yl]-3-nitrobenzene-1,2-diol or a pharmaceutically acceptable salt thereof, wherein the compound is administered in combination with a therapeutically effective amount of levodopa.

2. The method according to claim 1, wherein the compound is administered from 0.25 to 12 hours after an intake of food.

3. The method according to claim 1, wherein the compound is administered from 0.25 to 2 hours before an intake of food.

4. The method according to claim 1, wherein the compound is administered less than one hour prior to sleep, less than one hour before bedtime or at bedtime.

5. The method according to claim 1, wherein the compound is administered at least one hour after the most recent intake of food and at least one hour before the next intake of food by the patient.

6. The method according to claim 1, wherein the compound is administered in a single daily dose.

7. The method according to claim 1, wherein the compound is administered before or after levodopa.

8. The method according to claim 7, wherein the compound is administered from 30 to 150 minutes before or after levodopa.

9. The method according to claim 1, wherein the compound is administered at least one hour before or after the last daily dose levodopa.

10. The method according to claim 1, wherein levodopa is administered sequentially or concomitantly with an aromatic L-amino acid decarboxylase inhibitor (AADCi).

11. The method according to claim 10, wherein the AADCi is carbidopa or benserazide.

12. The method according to claim 2, wherein the compound is administered from 0.5 to 6 hours after an intake of food.

13. The method according to claim 2, wherein the compound is administered from 0.75 to 4 hours after an intake of food.

14. The method according to claim 3, wherein the compound is administered from 0.5 to 1.5 hours before an intake of food.

15. The method according to claim 1, wherein 50 mg of the compound is administered in each dosing periodicity.

16. The method according to claim 1, wherein 25 mg of the compound is administered in each dosing periodicity.

17. The method according to claim 1, wherein the 5-[3-(2,5-dichloro-4,6-dimethyl-1-oxy-pyridin-3-yl)-[1,2,4]oxadiazol-5-yl]-3-nitrobenzene-1,2-diol or pharmaceutically acceptable salt thereof is administered orally as a solid form.

* * * * *